United States Patent
Law et al.

(10) Patent No.: US 10,973,821 B2
(45) Date of Patent: Apr. 13, 2021

(54) PHARMACEUTICAL FORMULATION

(71) Applicant: F2G LIMITED, Manchester (GB)

(72) Inventors: Derek Law, Manchester (GB); Graham Edward Morris Sibley, Manchester (GB)

(73) Assignee: F2G LIMITED, Manchester (GB)

( * ) Notice: Subject to any disclaimer, the term of this patent is extended or adjusted under 35 U.S.C. 154(b) by 114 days.

(21) Appl. No.: 16/303,999

(22) PCT Filed: May 25, 2017

(86) PCT No.: PCT/GB2017/051494
§ 371 (c)(1),
(2) Date: Nov. 21, 2018

(87) PCT Pub. No.: WO2017/203270
PCT Pub. Date: Nov. 30, 2017

(65) Prior Publication Data
US 2019/0328737 A1    Oct. 31, 2019

(30) Foreign Application Priority Data
May 25, 2016 (GB) ..................... 1609222

(51) Int. Cl.
| A61K 31/506 | (2006.01) |
| A61P 31/10 | (2006.01) |
| A61K 9/00 | (2006.01) |
| A61K 9/19 | (2006.01) |
| A61K 47/32 | (2006.01) |
| A61K 47/34 | (2017.01) |
| A61K 47/40 | (2006.01) |

(52) U.S. Cl.
CPC .......... *A61K 31/506* (2013.01); *A61K 9/0053* (2013.01); *A61K 9/19* (2013.01); *A61K 47/32* (2013.01); *A61K 47/34* (2013.01); *A61K 47/40* (2013.01); *A61P 31/10* (2018.01)

(58) Field of Classification Search
None
See application file for complete search history.

(56) References Cited

U.S. PATENT DOCUMENTS

| 3,202,654 | A | 8/1965 | Gaston |
| 3,252,970 | A | 5/1966 | Ferdinand |
| 3,256,279 | A | 6/1966 | George |
| 3,458,515 | A | 7/1969 | Archibald |
| 3,573,294 | A | 3/1971 | Long |
| 3,857,857 | A | 12/1974 | Bella |
| 4,148,907 | A | 4/1979 | Conti |
| 4,163,015 | A | 7/1979 | Johnson |
| 4,316,900 | A | 2/1982 | Wasley |
| 4,761,424 | A | 8/1988 | Carethers |
| 4,794,120 | A | 12/1988 | Manoury |
| 5,750,540 | A | 5/1998 | Tsuchiya |
| 6,645,976 | B1 | 11/2003 | Dillard |
| 7,780,988 | B2 | 8/2010 | Beyerinck |
| 8,524,705 | B2 | 9/2013 | Payne |
| 8,617,604 | B2 | 12/2013 | Babcock |
| 8,741,346 | B2 | 6/2014 | Lochard |
| 8,828,443 | B2 | 9/2014 | Beyerinck |
| 8,940,800 | B2 | 1/2015 | Babcock |
| 8,993,574 | B2 | 3/2015 | Sibley |
| 9,040,033 | B2 | 5/2015 | Miller |
| 9,452,168 | B2 | 9/2016 | Sibley |
| 10,201,524 | B2 * | 2/2019 | Sibley ................ A61K 31/4025 |
| 10,596,150 | B2 * | 3/2020 | Sibley .................... A61P 11/06 |
| 2005/0032871 | A1 | 2/2005 | Tang |
| 2005/0090541 | A1 | 4/2005 | Arnaiz |
| 2006/0058286 | A1 | 3/2006 | Krystal |
| 2008/0118500 | A1 | 5/2008 | Liu |
| 2015/0273354 | A1 | 10/2015 | Dobry |
| 2017/0340607 | A1 | 11/2017 | Sibley |

FOREIGN PATENT DOCUMENTS

| DE | 2253150 A1 | 5/1973 |
| DE | 2429923 A1 | 1/1975 |
| DE | 2751571 A1 | 5/1978 |
| EA | 200101172 A1 | 4/2002 |
| EP | 0252809 A2 | 1/1988 |
| EP | 0505321 A2 | 9/1992 |
| EP | 0747756 A1 | 12/1996 |
| EP | 0901786 A2 | 3/1999 |
| EP | 1239835 A1 | 9/2002 |
| EP | 1543841 A1 | 6/2005 |
| EP | 1027887 B1 | 8/2008 |
| EP | 1886673 B1 | 10/2011 |

(Continued)

OTHER PUBLICATIONS

Harald published Sep. 29, 2015, (Year: 2015).*
Dorby et al. "A Model-Based Methodology for Spray-Drying Process Development," J Pharm Innov (2009) 4:133-142. (Year: 2009).*
Alvarez, M. et al. (1999). "Synthesis of 1,2-Dihydropyrrolo[1,2-c]Pyrimidin-1-Ones," Journal of Chemical Society pp. 249-255.
Alves, M.J. et al. (2000). "Novel Aziridine Esters by the Addition of Aromatic Nitrogen Heterocycles to a 2H-Azirine-3-Carboxylic Ester," Tetrahedron Letters 41:4991-4995.
Ames, D.E. et al. (1959, e-pub. Jan. 1, 1959). "The Preparation of Aminoalkylpyrrocolines," Journal of Chemical Society 124:620-622.

(Continued)

Primary Examiner — Jeffrey S Lundgren
Assistant Examiner — Michael J Schmitt
(74) Attorney, Agent, or Firm — Morrison & Foerster LLP

(57) ABSTRACT

A pharmaceutical composition suitable for oral administration comprising particles of 2-(1,5-dimethyl-3-phenyl-1H-pyrrol-2-yl)-N-(4-(4-(5-fluoropyrimidin-2-yl)piperazin-1-yl)phenyl)-2- oxoacetamideis provided. Also provided is a pharmaceutical composition suitable for parenteral administration wherein the composition comprises 2-(1,5-dimethyl-3-phenyl-1H-pyrrol-2-yl)-N-(4-(4-(5-fluoropyrimidin-2-yl)piperazin-1-yl)phenyl)-2-oxoacetamide. The compositions are useful in the treatment of fungal infection in a subject in need thereof.

17 Claims, 2 Drawing Sheets

(56) References Cited

FOREIGN PATENT DOCUMENTS

| | | | |
|---|---|---|---|
| EP | 1653928 | B1 | 3/2012 |
| EP | 2529731 | A1 | 12/2012 |
| EP | 2636409 | A1 | 9/2013 |
| FR | 1381256 | A | 12/1964 |
| FR | 1556822 | A | 2/1969 |
| GB | 1051723 | A | 12/1966 |
| GB | 1208014 | A | 10/1970 |
| GB | 1476503 | A | 6/1977 |
| JP | 57142966 | A | 9/1982 |
| JP | 57144255 | A | 9/1982 |
| JP | 62081369 | A | 4/1987 |
| JP | 09249669 | A | 9/1997 |
| RU | 2152392 | C1 | 7/2000 |
| WO | WO199601822 | A1 | 1/1996 |
| WO | WO199603383 | A1 | 2/1996 |
| WO | WO199633973 | A1 | 10/1996 |
| WO | WO199856422 | A1 | 12/1998 |
| WO | WO199962881 | A1 | 12/1999 |
| WO | WO200032588 | A2 | 6/2000 |
| WO | WO200066580 | A2 | 11/2000 |
| WO | WO200108572 | A1 | 2/2001 |
| WO | WO200147495 | A1 | 7/2001 |
| WO | WO200185723 | A1 | 11/2001 |
| WO | WO2002085301 | A2 | 10/2002 |
| WO | WO2002085907 | A1 | 10/2002 |
| WO | WO2002098876 | A1 | 12/2002 |
| WO | WO2003000680 | A1 | 1/2003 |
| WO | WO2003064397 | A1 | 8/2003 |
| WO | WO2003072028 | A2 | 9/2003 |
| WO | WO2004082606 | A2 | 9/2004 |
| WO | WO2006105289 | A1 | 10/2006 |
| WO | WO2006113875 | A2 | 10/2006 |
| WO | WO2006123145 | A1 | 11/2006 |
| WO | WO2007009083 | A2 | 1/2007 |
| WO | WO2007015866 | A2 | 2/2007 |
| WO | WO2007009083 | A3 | 7/2007 |
| WO | WO2007109605 | A2 | 9/2007 |
| WO | WO2007109605 | A3 | 1/2008 |
| WO | WO2008062182 | A1 | 5/2008 |
| WO | WO2008092057 | A2 | 7/2008 |
| WO | WO2008092057 | A3 | 9/2008 |
| WO | WO2008106860 | A1 | 9/2008 |
| WO | WO2008145963 | A1 | 12/2008 |
| WO | WO2009010842 | A2 | 1/2009 |
| WO | WO2009010842 | A3 | 3/2009 |
| WO | WO2009130481 | A1 | 10/2009 |
| WO | WO2009144473 | A1 | 12/2009 |
| WO | WO2010045281 | A2 | 4/2010 |
| WO | WO2010045281 | A3 | 8/2010 |
| WO | WO2010126967 | A1 | 11/2010 |
| WO | WO2012060448 | A1 | 5/2012 |
| WO | WO2013078500 | A1 | 6/2013 |
| WO | WO2013154607 | A1 | 10/2013 |
| WO | WO2014031418 | A1 | 2/2014 |
| WO | WO2014031422 | A1 | 2/2014 |
| WO | WO2014114575 | A1 | 7/2014 |
| WO | WO2015007759 | A1 | 1/2015 |
| WO | WO2015007760 | A1 | 1/2015 |
| WO | WO2015082562 | A1 | 6/2015 |
| WO | WO2015150763 | A1 | 10/2015 |
| WO | WO2016079536 | A1 | 5/2016 |

OTHER PUBLICATIONS

Anonymous (Sep. 4, 2014). "F2G Begins F901318 Phase I Clinical Study for Treatment of Aspergillus Infections", News Medical Life Sciences, Sep. 4, 2014, retrieved from URL:http://www.news-medical.net/news/20140904/F2G-begins-F901318-Phase-I-clinical-study-for-treatment-of-aspergillus-infections.aspx, 2 pages.
Anonymous (Sep. 17, 2017). "In Vivo Efficacy of Orally Dosed F901318, in a Murine Model of Disseminated Aspergillosis", 55th Intersci Conf Antimicrob Agents Chemother (ICAAC), retrieved from the Internet: URL:https://integrity.thomson-pharma.com/integrity/xmlxs1/pk_ref_listxml_show_ficha_ref?p_ref_id=2393484, last visited Nov. 7, 2017, 1 page.
Anonymous. (2012). "Diethyl Ether," retrieved from http:www.merckmillipore.com/chemicals/diethyl-ether/MDA_CHEM-100926/p_NgGb.s1Lay4AAAEW8uEfVhTI, last visited on Jul. 11, 2012, 4 pages.
Anonymous. (Mar. 2006-Nov. 2013), "Anacor Pharmaceuticals Scientific Presentations", 7 pages.
Archibald, J.L. et al. (1974). "Benzamidopiperidines. 2. Heterocyclic Compounds Related to Indoramin," Journal of Medicinal Chemistry 17(7):736-739.
Archibald, J.L. et al. (Sep. 1967). "New Reactions of Pyrroles. II. Preparation and Reactions of Pyrroleglyoxyloyl Derivatives," Journal of Heterocyclic Chemistry 4:335-338.
Battersby, A.R. et al. (1992, e-pub, Jan. 1, 1992). "Synthetic Studies Relevant to Biosynthetic Research on Vitamin B12. Part 10. Construction of the East and West Building Blocks for Synthesis of Isobacteriochlorins," Journal of Chemical Society 17:2175-2187.
Bentov, M. et al. (1964). "4-Fluoroindole and Derivatives," Israel Journal of Chemistry 2:25-28.
Birchall, G.R. et al. (1971). "The Chlorination of Pyrroles. Part II," Canadian Journal of Chemistry 49:919-922.
Black, D.S.C. et al. (1996). "Reaction of Some 4,6-Dimethoxyindoles with Oxalyl Chloride," Tetrahedron 52 (26):8925-8936.
Black, D.S.C. et al. (1996). "The Indol-2-Ylglyoxylamide Moiety: A New Building Block for the Design and Self-Assembly of Hydrogen Bond Networks," Journal of American Chemical Society 118(34):8148-8149.
Black, D.S.C. et al. (2000). "Formation of C-Amido-Calix[3]Indoles from 2'- and 7'-Indolylglyoxylamides," Tetrahedron 56:8513-8524.
Bohusch, M. et al. (1991). "Consequences of a Diminution of the Porphyrin π-System: Attempted Syntheses of Bacteriophin and Chlorophin," Liebigs Annalen der Chemie pp. 67-70. (English Abstract Only).
Borthwick, A.D. et al. (Jan. 3, 2002, e-pub. Dec. 5, 2001). "Design and synthesis of Pyrrolidine-5,5-trans-Lactams (5-Oxohexahdropyrrolo[3,2-b]Pyrroles) as Novel Mechanism-Based Inhibitors of Human Cytomegalovirus Protease. 2. Potency and Chirality," Journal of Medicinal Chemistry 45(1):1-18.
Cameron, B.D. et al. (1973). "The Synthesis and Metabolic Fate of 14C-Viminol, a New Analgesic, in the Rat and the Dog," Arzneimittel-Forshung/Drug Res. 23(5):708-712.
Cardellini, M. et al. (Feb. 1977). "Indolizine Derivatives with Biological Activity I: N'-Substituted Hydrazides of Indolizine-2-Carboxylic Acid," Journal of Pharmaceutical Sciences 66(2):259-262.
CAS Registry No. 1002010-45-8, created Feb. 7, 2008, last accessed Oct. 30, 2013, 1 page.
CAS Registry No. 1002010-93-6, created Feb. 7, 2008, last accessed Oct. 30, 2013, 2 pages.
CAS Registry No. 1004172-59-1, created Feb. 18, 2008, last accessed Oct. 30, 2013, 1 page.
CAS Registry No. 1004425-72-2, created Feb. 19, 2008, last accessed Oct. 30, 2013, 1 page.
CAS Registry No. 1026853-99-5 created Jun. 9, 2008, last accessed Feb. 2, 2012, 1 page.
CAS Registry No. 1027826-94-3, created Jun. 9, 2008, last accessed Feb. 2, 2012, 1 page.
CAS Registry No. 1029775-76-5, created Jun. 22, 2008, last accessed Feb. 2, 2012, 2 pages.
CAS Registry No. 1056748-82-3, created Oct. 3, 2008, last accessed Feb. 2, 2012, 1 page.
CAS Registry No. 130761-64-7, created Nov. 30, 1990, last accessed Feb. 2, 2012, 1 page.
CAS Registry No. 130761-68-1, created Nov. 30, 1990, last accessed Feb. 2, 2012, 2 pages.
CAS Registry No. 145045-69-8, created Dec. 25, 1992, last accessed Feb. 2, 2012, 2 pages.
CAS Registry No. 15940-17-7, created Nov. 16, 1984, last accessed Feb. 2, 2012, 1 page.
CAS Registry No. 15940-18-8, created Nov. 16, 1984, last accessed Feb. 2, 2012, 1 page.

(56) References Cited

OTHER PUBLICATIONS

CAS Registry No. 15940-19-9, created Nov. 16, 1984, last accessed Feb. 2, 2012, 1 page.
CAS Registry No. 15940-20-2, created Nov. 16, 1984, last accessed Feb. 2, 2012, 2 pages.
CAS Registry No. 15940-21-3, created Nov. 16, 1984 last accessed Feb. 2, 2012, 1 page.
CAS Registry No. 15940-22-4, created Nov. 16, 1984, last accessed Feb. 2, 2012, 2 pages.
CAS Registry No. 15940-23-5, created Nov. 16, 1984, last accessed Feb. 2, 2012, 1 page.
CAS Registry No. 15940-24-6, created Nov. 16, 1984, last accessed Feb. 2, 2012, 2 pages.
CAS Registry No. 15940-25-7, created Nov. 16, 1984, last accessed Feb. 2, 2012, 1 page.
CAS Registry No. 171845-45-8, created Dec. 29, 1995, last accessed Feb. 2, 2012, 2 pages.
CAS Registry No. 171854-40-3, created Dec. 29, 1995, last accessed Feb. 2, 2012, 1 page.
CAS Registry No. 171854-41-4, created Dec. 29, 1995, last accessed Feb. 2, 2012, 2 pages.
CAS Registry No. 171854-42-5, created Dec. 29, 1995, last accessed Feb. 2, 2012, 2 pages.
CAS Registry No. 171854-43-6, created Dec. 29, 1995, last accessed Feb. 2, 2012, 2 pages.
CAS Registry No. 171854-44-7, created Dec. 29, 1995, last accessed Feb. 2, 2012, 1 page.
CAS Registry No. 171854-46-9, created Dec. 29, 1995, last accessed Feb. 2, 2012, 1 page.
CAS Registry No. 171854-47-0, created Dec. 29, 1995, last accessed Feb. 2, 2012, 2 pages.
CAS Registry No. 185030-21-1, created Jan. 15, 1997, last accessed Feb. 2, 2012, 1 page.
CAS Registry No. 208765-70-2, created Jul. 22, 1998, last accessed Feb. 2, 2012, 1 page.
CAS Registry No. 208765-71-3, created Jul. 22, 1998, last accessed Feb. 2, 2012, 1 page.
CAS Registry No. 208765-72-4, created Jul. 22, 1998, last accessed Feb. 2, 2012, 2 pages.
CAS Registry No. 208765-73-5, created Jul. 22, 1998, last accessed Feb. 2, 2012, 1 page.
CAS Registry No. 208765-74-6, created Jul. 22, 1998, last accessed Feb. 2, 2012, 1 page.
CAS Registry No. 208765-75-7, created Jul. 22, 1998, last accessed Feb. 2, 2012, 1.
CAS Registry No. 208765-76-8, created Jul. 22, 1998, last accessed Feb. 2, 2012, 1 page.
CAS Registry No. 208765-77-9, created Jul. 22, 1998, last accessed Feb. 2, 2012, 2 pages.
CAS Registry No. 208765-78-0, created Jul. 22, 1998, last accessed Feb. 2, 2012, 1 page.
CAS Registry No. 208765-79-1, created Jul. 22, 1998, last accessed Feb. 2, 2012, 2 pages.
CAS Registry No. 208765-80-4, created Jul. 22, 1998, last accessed Feb. 2, 2012, 1 page.
CAS Registry No. 208765-81-5, created Jul. 22, 1998, last accessed Feb. 2, 2012, 2 pages.
CAS Registry No. 208765-82-6, created Jul. 22, 1998, last accessed Feb. 2, 2012, 1 page.
CAS Registry No. 208765-83-7, created Jul. 22, 1998, last accessed Feb. 2, 2012, 2 pages.
CAS Registry No. 208765-84-8, created Jul. 22, 1998, last accessed Feb. 2, 2012, 1 page.
CAS Registry No. 208765-85-9, created Jul. 22, 1998, last accessed Feb. 2, 2012, 2 pages.
CAS Registry No. 208765-86-0, created Jul. 22, 1998, last accessed Feb. 2, 2012, 1 page.
CAS Registry No. 208765-87-1, created Jul. 22, 1998, last accessed Feb. 2, 2012, 2 pages.
CAS Registry No. 208765-88-2, created Jul. 22, 1998, last accessed Feb. 2, 2012, 1 page.
CAS Registry No. 208765-89-3, created Jul. 22, 1996, last accessed Feb. 2, 2012, 2 pages.
CAS Registry No. 208765-90-6, created Jul. 22, 1998, last accessed Feb. 2, 2012, 1 page.
CAS Registry No. 208765-91-7, created Jul. 22, 1998, last accessed Feb. 2, 2012, 1 page.
CAS Registry No. 208765-92-8, created Jul. 22, 1998, last accessed Feb. 2, 2012, 1 page.
CAS Registry No. 208765-93-9, created Jul. 22, 1998, last accessed Feb. 2, 2012, 1 page.
CAS Registry No. 208765-94-0, created Jul. 22, 1998, last accessed Feb. 2, 2012, 2 pages.
CAS Registry No. 208765-95-1, created Jul. 22, 1998, last accessed Feb. 2, 2012, 1 page.
CAS Registry No. 208765-96-2, created Jul. 22, 1998, last accessed Feb. 2, 2012, 2 pages.
CAS Registry No. 208766-03-4, created Jul. 22, 1998, last accessed Feb. 2, 2012, 1 page.
CAS Registry No. 208766-04-5, created Jul. 22, 1998, last accessed Feb. 2, 2012, 2 pages.
CAS Registry No. 208766-05-6, created Jul. 22, 1998, last accessed Feb. 2, 2012, 1 page.
CAS Registry No. 23502-48-9, created Nov. 16, 1984, last accessed Feb. 2, 2012, 2 pages.
CAS Registry No. 263554-36-5, created May 2, 2000, last accessed Feb. 2, 2012, 1 page.
CAS Registry No. 263554-39-8, created May 2, 2000, last accessed Feb. 2, 2012, 2 pages.
CAS Registry No. 26883-51-2, created Nov. 16, 1984, last accessed Feb. 2, 2012, 1 page.
CAS Registry No. 292063-96-8, created Oct. 2, 2000, last accessed Feb. 2, 2012, 1 page.
CAS Registry No. 292064-15-4, created Oct. 2, 2000, last accessed Feb. 2, 2012, 2 pages.
CAS Registry No. 31709-75-8, created Nov. 16, 1984, last accessed Feb. 2, 2012, 2 pages.
CAS Registry No. 31709-76-9, created Nov. 16, 1984, last accessed Feb. 2, 2012, 1 page.
CAS Registry No. 31709-77-0, created Nov. 16, 1984, last accessed Feb. 2, 2012, 1 page.
CAS Registry No. 31710-23-3, created Nov. 16, 1984, last accessed Feb. 2, 2012, 1 page.
CAS Registry No. 364044-26-8, created Oct. 23, 2001, last accessed Feb. 2, 2012, 1 page.
CAS Registry No. 364044-30-4, created Oct. 23, 2001, last accessed Feb. 2, 2012, 2 pages.
CAS Registry No. 36793-47-2, created Nov. 16, 1984, last accessed Feb. 2, 2012, 2 pages.
CAS Registry No. 3758-62-1, created Nov. 16, 1984, last accessed Feb. 2, 2012, 1 page.
CAS Registry No. 3768-71-6, created Nov. 16, 1984, last accessed Feb. 2, 2012, 1 page.
CAS Registry No. 3768-72-7, created Nov. 16, 1984, last accessed Feb. 2, 2012, 1 page.
CAS Registry No. 3768-82-9, created Nov. 16, 1984, last accessed Feb. 2, 2012, 2 pages.
CAS Registry No. 396733-55-4, created Feb. 28, 2002, last accessed Feb. 2, 2012, 1 page.
CAS Registry No. 41596-37-6, created Nov. 16, 1984, last accessed Feb. 2, 2012, 1 page.
CAS Registry No. 42060-03-7, created Nov. 16, 1984, last accessed Feb. 2, 2012, 2 pages.
CAS Registry No. 42060-05-9, created Nov. 16, 1984, last accessed Feb. 2, 2012, 1 page.
CAS Registry No. 42221-74-9, created Nov. 16, 1984, last accessed Feb. 2, 2012, 2 pages.
CAS Registry No. 422507-64-0, created May 29, 2002, last accessed Feb. 2, 2012, 1 page.
CAS Registry No. 422507-66-2, created May 29, 2002, last accessed Feb. 2, 2012, 1 page.

(56) References Cited

OTHER PUBLICATIONS

CAS Registry No. 422507-69-5, created May 29, 2002, last accessed Feb. 2, 2012, 1 page.
CAS Registry No. 43084-49-7, created Nov. 16, 1984, last accessed Feb. 2, 2012, 1 page.
CAS Registry No. 4380-46-5, created Nov. 16, 1984, last accessed Feb. 2, 2012, 1 page.
CAS Registry No. 4595-83-9, created Nov. 16, 1984, last accessed Feb. 2, 2012, 2 pages.
CAS Registry No. 477709-20-9, created Dec. 27, 2002, last accessed Feb. 2, 2012, 2 pages.
CAS Registry No. 477709-21-0, created Dec. 27, 2002 last accessed Feb. 2, 2012, 2 pages.
CAS Registry No. 477709-22-1, created Dec. 27, 2002, last accessed Feb. 2, 2012, 1 page.
CAS Registry No. 477709-24-3, created Dec. 27, 2002, last accessed Feb. 2, 2012, 2 pages.
CAS Registry No. 477709-25-4, created Dec. 27, 2002, last accessed Feb. 2, 2012, 1 page.
CAS Registry No. 477709-26-5, created Dec. 27, 2002, last accessed Feb. 2, 2012, 2 pages.
CAS Registry No. 477709-27-6, created Dec. 27, 2002, last accessed Feb. 2, 2012, 1 page.
CAS Registry No. 477709-28-7, created Dec. 27, 2002, last accessed Feb. 2, 2012, 2 pages.
CAS Registry No. 477709-29-8, created Dec. 27, 2002, last accessed Feb. 2, 2012, 1 page.
CAS Registry No. 477709-30-1 created Dec. 27, 2002, last accessed Feb. 2, 2012, 2 pages.
CAS Registry No. 477857-72-0, created Dec. 31, 2002, last accessed Feb. 2, 2012, 1 page.
CAS Registry No. 477857-73-1, created Dec. 31, 2002, last accessed Feb. 2, 2012, 2 pages.
CAS Registry No. 477857-74-2, created Dec. 31, 2002, last accessed Feb. 2, 2012, 1 page.
CAS Registry No. 477857-75-3, created Dec. 31, 2002, last accessed Feb. 2, 2012, 2 pages.
CAS Registry No. 477857-76-4, created Dec. 31, 2002, last accessed Feb. 2, 2012, 1 page.
CAS Registry No. 477857-77-5, created Dec. 31, 2002, last accessed Feb. 2, 2012, 2 pages.
CAS Registry No. 477857-78-6; created Dec. 31, 2002, last accessed Feb. 2, 2012, 1 page.
CAS Registry No. 477857-79-7, created Dec. 31, 2002, last accessed Feb. 2, 2012, 2 pages.
CAS Registry No. 477857-80-0, created Dec. 31, 2002, last accessed Feb. 2, 2012, 1 page.
CAS Registry No. 477857-81-1, created Dec. 31, 2002, last accessed Feb. 2, 2012, 2 pages.
CAS Registry No. 477863-31-3, created Dec. 31, 2002, last accessed Feb. 2, 2012, 1 page.
CAS Registry No. 477863-34-6, created Dec. 31, 2002, last accessed Feb. 2, 2012, 2 pages.
CAS Registry No. 477863-37-9, created Dec. 31, 2002, last accessed Feb. 2, 2012, 1 page.
CAS Registry No. 477871-94-6, created Dec. 31, 2002, last accessed Feb. 2, 2012, 2 pages.
CAS Registry No. 477871-95-7, created Dec. 31, 2002, last accessed Feb. 2, 2012, 1 page.
CAS Registry No. 477871-96-8, created Dec. 31, 2002, last accessed Feb. 2, 2012, 1 page.
CAS Registry No. 477871-97-9, created Dec. 31, 2002, last accessed Feb. 2, 2012, 1 page.
CAS Registry No. 477871-98-0, created Dec. 31, 2002, last accessed Feb. 2, 2012, 1 page.
CAS Registry No. 477871-99-1 created Dec. 31, 2002, last accessed Feb. 2, 2012, 2 pages.
CAS Registry No. 477872-00-7, created Dec. 31, 2002, last accessed Feb. 2, 2012, 1 page.
CAS Registry No. 477872-01-8, created Dec. 31, 2002, last accessed Feb. 2, 2012, 2 pages.
CAS Registry No. 477872-02-9, created Dec. 31, 2002, last accessed Feb. 2, 2012, 1 page.
CAS Registry No. 477872-03-0, created Dec. 31, 2002, last accessed Feb. 2, 2012, 1 page.
CAS Registry No. 477872-04-1, created Dec. 31, 2002, last accessed Feb. 2, 2012, 2 pages.
CAS Registry No. 477872-05-2, created Dec. 31, 2002, last accessed Feb. 2, 2012, 1 page.
CAS Registry No. 477872-69-8, created Dec. 31, 2002, last accessed Feb. 2, 2012, 2 pages.
CAS Registry No. 477872-70-1, created Dec. 31, 2002, last accessed Feb. 2, 2012, 1 page.
CAS Registry No. 477872-71-2, created Dec. 31, 2002, last accessed Feb. 2, 2012, 2 pages.
CAS Registry No. 477872-72-3, created Dec. 31, 2002, last accessed Feb. 2, 2012, 1 page.
CAS Registry No. 477872-73-4 created Dec. 31, 2002, last accessed Feb. 2, 2012, 2 pages.
CAS Registry No. 477872-74-5, created Dec. 31, 2002, last accessed Feb. 2, 2012, 1 page.
CAS Registry No. 477872-75-6, created Dec. 31, 2002, last accessed Feb. 2, 2012, 2 pages.
CAS Registry No. 477872-76-7, created Dec. 31, 2002, last accessed Feb. 2, 2012, 1 page.
CAS Registry No. 477872-77-8, created Dec. 31, 2002, last accessed Feb. 2, 2012, 1 page.
CAS Registry No. 477872-78-9, created Dec. 31, 2002, last accessed Feb. 2, 2012, 2 pages.
CAS Registry No. 477872-79-0, created Dec. 31, 2002, last accessed Feb. 2, 2012, 1 page.
CAS Registry No. 477872-80-3, created Dec. 31, 2002, last accessed Feb. 2, 2012, 2 pages.
CAS Registry No. 485843-91-2, created Feb. 5, 2003, last accessed Feb. 2, 2012, 1 page.
CAS Registry No. 485843-92-3, created Feb. 5, 2003, last accessed Feb. 2, 2012, 1 page.
CAS Registry No. 53391-28-9, created Nov. 16, 1984, last accessed Feb. 2, 2012, 2 pages.
CAS Registry No. 53391-29-0, created Nov. 16, 1984, last accessed Feb. 2, 2012, 1 page.
CAS Registry No. 53391-30-3, created Nov. 16, 1984, last accessed Feb. 2, 2012, 2 pages.
CAS Registry No. 53391-52-9, created Nov. 16, 1984, last accessed Feb. 2, 2012, 1 page.
CAS Registry No. 53391-63-2, created Nov. 16, 1984, last accessed Feb. 2, 2012, 2 pages.
CAS Registry No. 65473-58-7, created Nov. 16, 1984, last accessed Feb. 2, 2012, 1 page.
CAS Registry No. 655223-84-0, created Feb. 27, 2004, last accessed Feb. 2, 2012, 1 page.
CAS Registry No. 655223-85-1, created Feb. 27, 2004 last accessed Feb. 2, 2012, 2 pages.
CAS Registry No. 6616-51-9, created Nov. 16, 1984, last accessed Feb. 2, 2012, 1 page.
CAS Registry No. 68803-72-5, created Nov. 16, 1984, last accessed Feb. 2, 2012, 2 pages.
CAS Registry No. 773098-60-5, created Nov. 1, 2004, last accessed Feb. 2, 2012, 1 page.
CAS Registry No. 773098-61-6, created Nov. 1, 2004, last accessed Feb. 2, 2012, 2 pages.
CAS Registry No. 802313-56-0, created Dec. 25, 2004, last accessed Feb. 2, 2012, 1 page.
CAS Registry No. 81729-69-3, created Nov. 16, 1984, last accessed Feb. 2, 2012, 1 page.
CAS Registry No. 81741-58-4, created Nov. 16, 1984, last accessed Feb. 2, 2012, 1 page.
CAS Registry No. 83996-64-9, created Nov. 16, 1984, last accessed Feb. 2, 2012, 1 page.
CAS Registry No. 860610-36-2, created Aug. 17, 2005, last accessed Feb. 2, 2012, 1 page.

(56) References Cited

OTHER PUBLICATIONS

CAS Registry No. 860610-37-3, created Aug. 17, 2005, last accessed Feb. 2, 2012, 1 page.
CAS Registry No. 860649-79-2, created Aug. 17, 2005, last accessed Feb. 2, 2012, 1 page.
CAS Registry No. 860649-80-5, created Aug. 17, 2005, last accessed Feb. 2, 2012, 1 page.
CAS Registry No. 866010-45-9, created Oct. 25, 2005, last accessed Feb. 2, 2012, 1 page.
CAS Registry No. 866010-46-0, created Oct. 25, 2005, last accessed Feb. 2, 2012, 2 pages.
CAS Registry No. 866010-47-1, created Oct. 25, 2005, last accessed Feb. 2, 2012, 1 page.
CAS Registry No. 866010-76-6, created Oct. 25, 2005, last accessed Feb. 2, 2012, 2 pages.
CAS Registry No. 866010-82-4, created Oct. 25, 2005, last accessed Feb. 2, 2012, 1 page.
CAS Registry No. 866010-83-5, created Oct. 25, 2005, last accessed Feb. 2, 2012, 2 pages.
CAS Registry No. 866010-85-7, created Oct. 25, 2005, last accessed Feb. 2, 2012, 1 page.
CAS Registry No. 866042-95-7, created Oct. 25, 2005, last accessed Feb. 2, 2012, 1 page.
CAS Registry No. 866042-98-0, created Oct. 25, 2005, last accessed Feb. 2, 2012, 1 page.
CAS Registry No. 866042-99-1, created Oct. 25, 2005, last accessed Feb. 2, 2012, 1 page.
CAS Registry No. 866043-03-0, created Oct. 25, 2005, last accessed Feb. 2, 2012, 2 pages.
CAS Registry No. 866043-06-3, created Oct. 25, 2005, last accessed Feb. 2, 2012, 1 page.
CAS Registry No. 945220-52-0, created Aug. 21, 2007, last accessed Feb. 2, 2012, 1 page.
CDC. (Nov. 16, 2015). "Aspergillosis Risk and Prevention," retrieved from http://www.cdc.fungal/diseases/aspergillosis/risk-prevention.html, last visited Nov. 16, 2015, 3 pages.
CDC. (Nov. 16, 2015). "Fungal Diseases," retrieved from http://www.cdc.fungal/diseases/aspergillosis/risk-prevention.html, last visited Nov. 16, 2015, 2 pages.
Chemcats. (Feb. 13, 2008). "1H-Pyrrole-2-Acetamide, N-(4-Bromophenyl)-1-(2-Chloro-4-Nitrophenyl)-α-Oxo-," Ambinter Stock Screening Collection, 5 pages.
Chemcats. (Feb. 18, 2008). "1H-Pyrrole-2-Acetamide, N-(2,4-Dichlorophenyl)-1-Methyl-α-Oxo-," Interchim Intermediates 5 pages.
Chemcats. (Jan. 25, 2008). "Benzo [b] Thiophene-2-Carboxylic Acid, 3-[2-[[(4-Methoxyphenyl) Amino] Oxoacetyl]-1H-Pyrrol-1-yl]-, Methyl Ester," Ryan Scientific Screening Library 5 pages.
Chiarino, D. et al. (1978). "Stereochemistry of Viminol, a Novel Central Analgesic," Arzneimittel-Forshung/Drug Res. 28(11):1554-1561.
Cook, A.H. et al. (1949, e-pub. Jan. 1, 1949). "Studies in the Azole Series. Part XXIV. The Interaction of Carbonyl Compounds and 2-Thio-5-Thiazolidone," Journal of Chemical Society 633:3007-3012.
Crowley, K.J. et al. (1957). "Intermediates for the Synthesis of Optically Active Methyl-Substituted Long-Chain Acids. Part II," Journal of the Chemical Society 2931-2934.
Dannhardt, G. et al. (1979). "Synthese und Eigenschaften von 2,3-Dihydro-1H-Pyrrolizinen," Arch. Pharm. 312:896-907. (English Abstract).
Dannhardt, G. et al. (1994). "Nonsteroidal Antiinflammatory Agents, XVIII: C-5 Functionalized 6,7-Diphenyl-2,3-Dihydro-1H-Pyrrolizines as Inhibitors of Bovine Cyclooxygenase and 5-Lipoxygenase," Arch Pharm 327:509-514.
Dannhardt, V.G. et al. (1986). "Antiphlogistische 2,3-Dihydro-1H-Pyrrolizine, 11. Mitt. Dihydropyrrolizinyl-Substituierte 2-Aminoethanol- und Glykosäure-Derivate," Chemiker-Zeitung 110(3):124-127. (English Abstract).
Dumoulin, H. et al. (1998). "2-Oxo-2-(Pehn-2-Ylpyrrol-2-Yl)Acetamides as Potential Anxiolytic Agents: Synthesis and Affinity at the Central Benzodiazepine Receptor," European Journal of Medicinal Chemistry 33:201-207.
Dyke, S.F. et al. (1978). "Pavinane and Isopavinane Alkaloids," Tetrahedron 34:241-245.
Ertl, P. et al. (2000). "Fast Calculation of Molecular Polar Surface Area as a Sum of Fragment-Based Contributions and Its Application to the Prediction of Drug Transport Properties," J. Med. Chem. 43(20):3714-3717.
Fryer, R.I. et al. (Dec. 1967). "Quinazolines and 1,4-Benzodiazepines. XXXVII. Synthesis and Rearrangements of a Substituted 5-Phenyl-1H-1,4-Benzodiazepine," Journal of Organic Chemistry 32:3798-3803.
Galbraith, A. et al. (Jan. 20, 1961). "The Formation of Cycl[3,2,2]azine Derivatives via the Reaction of Pyrrocoline with Dimethyl Acetylenedicarboxylate," Journal of the American Chemical Society 83:453-458.
Groll, A.H. et al. (1996). "Trends in the Postmortem Epidemiology of Invasive Fungal Infections at a University Hospital," Journal of Infection 33:23-32.
Hagishita, S. et al. (1996). "Potent Inhibitors of Secretory Phospholipase A2: Synthesis and Inhibitory Activities of Indolizine and Indene Derivatives," Journal of Medicinal Chemistry 39(19):3636-3658.
Hudack, R.A. et al. (2006, e-pub. Jan. 14, 2006). "Design, Synthesis, and Biological Activity of Novel Polycyclic Aza-Amide FKBP12 Ligands," Journal of Medicinal Chemistry 49(3):1202-1206.
Ignatovich, J. et al. (2008). "Synthesis of Functionalized Benzyl Amines by the Reductive Alkylation of Heterocyclic and Heteroaromatic Amines with Arylaldehydes and preparation of the Intermediates for New Synthetic Biomolecules," ARKAT-USA, Inc. (ix):42-51.
Islam, I. et al. (2007, e-pub. Apr. 27, 2007). "Indolinone Based Phosphoinositide-Dependent Kinase-1 (PDK1) Inhibitors. Part 1: Design, Synthesis and Biological Activity," Bioorganic & Medicinal Chemistry Letters 17:3814-3818.
Keawin, T. et al. (2005, e-pub. Dec. 10, 2004), "Reaction of Some 4,6-Dimethoxyindoles with Nitric Acid: Nitration and Oxidative Dimerisation," Tetrahedron 61:853-861.
Leo, A. et al. (Dec. 1971). "Partition Coefficients and Their Uses," Chemical Reviews 71(6):525-616.
Mahiout, Z. et al. (2008, e-pub. Feb. 28, 2008). "Solvent-Dependent Oxidations of 5- and 6-Azaindoles to Trioxopyrrolopyridines and Functionalised Azaindoles," Organic & Biomolecular Chemistry 6:1364-1376.
Mao, W. et al. (Date Unknown) "AN2718 Has Broad Spectrum Antifungal Activity Necessary for the Topical Treatment of Skin and Nail Fungal Infections," P2422, 7 pages.
McDonell et al. (Jan. 1999). "Antiseptics and Disinfectants: Activity, Action, and Resistance," Clinical Microbiology Reviews 12(1):147-179.
Nourmohammadian, F. et al. (2005, e-pub. Jan. 21, 2005). "An AB Initio Molecular Orbital Study of Structural Isomers of Diketopyrrolopyrrole," Dyes and Pigments 67:15-20.
Plattner, J.J. et al. (Date Unknown). "Medicinal Chemistry of AN2690, A Novel Broad-Spectrum Antifungal Agent in Development for the Topical Treatment of Onychomycosis," Poster #775, Anacor Pharmaceuticals, 1 page.
Pätzel, M. et al. (2005). "Product Class 5: α-Heteroatom-Substituted Alkanamides," Science of Synthesis 21:477-535.
Ribaud, P. et al. (Feb. 1999). "Survival and Prognostic Factors of Invasive Aspergillosis After Allogeneic Bone Marrow Transplantation," Clinical Infectious Diseases 28:322-330.
Rowe, F.M. et al. (1935, e-pub. Jan. 1, 1935). "A Reaction of Certain Diazosulphonates Derived from β-Naphthol-1-Sulphonic Acid. Part XIII. Fission of the Naphthalene Nucleus and Subsequent Closure in Two Directions," Journal of Chemical Society 420:1796-1808.
Rowe, F.M. et al. (1936, e-pub. Jan. 1, 1936). "A Reaction of Certain Diazosulphonates Derived from β-Naphthol-1-Sulphonic Acid. Part XV. Derivatives of 2'-Nitro-4'-Methyl-Benzene-2-Naphthol-1-Diazosulphonate and Synthesis of 2-(2'-Nitro-4'-Methylphenylamino)Isoindolinone-3-Acetic Acid," Journal of Chemical Society 232:1098-1108.
Roy, K. et al. (Dec. 2008). "Development of Linear and Nonlinear Predictive QSAR Models and Their External Validation Using

(56) References Cited

OTHER PUBLICATIONS

Molecular Similarity Principle for Anti-HIV Indolyl Aryl Sulfones," Journal of Enzyme Inhibition and Medicinal Chemistry 23(6):980-995.

Savage, S.A. et al. (1998). "Efficient Synthesis of 4-, 5-, and 6-Methyl-2,2'-Bipyridine by a Negishi Cross-Coupling Strategy Followed by High-Yield Conversion to Bromo- and Chloromethyl-2,2'-Bipyridines," Journal of Organic Chemistry 63(26):10048-10051.

Schoichet Laboratory at UCSF (through ZINC database of commercially available small molecules—entered to CHEMCATS Feb. and Mar. 2008; p. 1-64.

Scott, M.K. et al. (1995). "Piperazinylalkyl Heterocycles as Potential Antipsychotic Agents," Journal of Medicinal Chemistry 38(21):4198-4210.

Si, Z. et al. (Apr. 6, 2004). "Small-Molecule Inhibitors of HIV-1 Entry Block Receptor-Induced Conformational Changes in the Viral Envelope Glycoproteins," Proceedings of the National Academy of Sciences 101(14):5036-5041.

Slassi, A. et al. (2000). "5-Alkyltryptamine Derivatives as Highly Selective and Potent 5-HT1D Receptor Agonists," Bioorganic & Medicinal Chemistry Letters 10:1707-1709.

Sofan, M.A. et al. (2004). "Studies on 2,3-Dioxopyrrolidines. Synthesis of Piperazine, Pyrrolo[4,5-b]Indole, Pyrazino [5,6-b]Indole and Arylazo Derivatives of Amino Acids," Polish Journal of Chemistry 78:837-842.

Troxler, F. et al. (1968). "Beiträge zur Chemie der Pyrrolo[3,2-c]Azepine und der Pyrrole[3,2-b]Azepine)," Helvetica Chimica Acta 51(8):1870-1880, (English Abstract).

Vecchietti, V. et al. (Jan.-Feb. 1974). "Nitro-Pyrrole Derivatives with Antimicrobial Activity," European Journal of Medicinal Chemistry 9(1):76-80.

Venturella, V.S. (Oct. 1964). "Arylindolizines III. Methoxyl and Glyoxyl Derivatives of Several Substituted Phenylindolizines," Journal of Pharmaceutical Sciences 53(10):1166-1169.

Wahyuningsih, T.D. et al. (2007, e-pub. May 3, 2007). "Synthesis of Indolo[2,3-c]Quinolines From 3-Arylindole-2-Ketoximes," Tetrahedron 63:6713-6719.

Yang, Z. et al. (2002). "A Strategy for the Synthesis of Aryl α-Ketoamides Based Upon the Acylation of Anions Derived from Cyanomethylamines Followed by Oxidative Cleavage," Organic Letters 4(7):1103-1105.

Yavari, I. et al. (2001). "Efficient Synthesis of 5,6,7-Trisubstituted 1H-Pyrrolizines," Tetrahedron 57:5873-5878.

Yavari, I. et al. (2002). "A Simple Synthesis of Stable Heterocyclic Phosphorus Ylides Derived from NH-Acids," Phosphorus, Sulfur and Silicon 177:545-553.

\* cited by examiner

PHARMACEUTICAL FORMULATION

CROSS-REFERENCE TO RELATED APPLICATIONS

This application is a U.S. national phase application under 35 U.S.C. § 371 of International Application No. PCT/GB2017/051494, filed May 25, 2017, which claims priority benefit of British Patent Application No. 1609222.3, filed May 25, 2016, the disclosures of each of which are hereby incorporated by reference in their entireties.

FIELD OF THE INVENTION

This invention relates to pharmaceutical formulations comprising a pyrrole compound. Specifically, it relates to pharmaceutical compositions which are suitable for oral administration, to pharmaceutical compositions which are suitable for parenteral administration, and to the use of such compositions in prevention or treatment of fungal diseases. It also relates to a method of producing a pharmaceutical composition as described herein.

BACKGROUND OF THE INVENTION

Invasive fungal infections are well recognised as diseases of the immunocompromised host. Over the last twenty years there have been significant rises in the number of recorded instances of fungal infection. In part this is due to increased awareness and improved diagnosis of fungal infection. However, the primary cause of this increased incidence is the vast rise in the number of susceptible individuals. This is due to a number of factors including new and aggressive immunosuppressive therapies, increased survival in intensive care, increased numbers of transplant procedures and the greater use of antibiotics worldwide.

In certain patient groups, fungal infection occurs at high frequency; lung transplant recipients have a frequency of up to 20% colonisation and infection with a fungal organism and fungal infection in allogenic haemopoetic stem cell transplant recipients is as high as 15% (Ribaud et al., 1999, *Clin Infect Dis.* 28:322-30).

Recently there has been increased awareness of the contribution of fungal sensitisation, colonisation, allergy and localised infection in the exacerbation of existing respiratory diseases. Here fungi have been implicated in asthma, COPD, brochiectasis and cystic fibrosis. Allergic bronchopulmonary aspergillosis (ABPA) is a lower respiratory tract condition caused by fungal colonisation, typically by *Apsergillus fumigatus*. ABPA can be seen in asthmatics at a rate of 0.7-3.5% and cystic fibrosis at a rate of 7-9%.

Currently there are four classes of antifungal drug are available to treat systemic fungal infections. These are the polyenes (e.g., amphotericin B), the azoles (e.g., ketoconazole or itraconazole), the echinocandins (e.g., caspofungin) and flucytosine.

The polyenes are the oldest class of antifungal agent being first introduced in the 1950's. The exact mode of action remains unclear but polyenes are only effective against organisms that contain sterols in their outer membranes. It has been proposed that amphotericin B interacts with membrane sterols to produce pores allowing leakage of cytoplasmic components and subsequent cell death.

Azoles work by inhibition of the 14a-demethylase via a cytochrome P450-dependent mechanism. This leads to a depletion of the membrane sterol ergosterol and the accumulation of sterol precursors resulting in a plasma membrane with altered fluidity and structure. Echinocandins work by the inhibition of the cell wall synthetic enzyme β-glucan synthase. This leads to abnormal cell wall formation, osmotic sensitivity and cell lysis.

Flucytosine is a pyrimidine analogue interfering with cellular pyrimidine metabolism as well DNA, RNA and protein synthesis. However widespread resistance to flucytosine limits its therapeutic use.

It can be seen that to date the currently available antifungal agents act primarily against only two cellular targets; membrane sterols (polyenes and azoles) and β-glucan synthase (echinocandins).

Resistance to both azoles and polyenes has been widely reported leaving only the recently introduced echinocandins to combat invasive fungal infections. As the use of echinocandins increases, resistance by fungi will inevitably occur.

The identification of new classes of antifungal agent is required to give the promise of positive therapeutic outcomes to patients.

Pyrrole compounds have also been identified as antifungal agents. WO 2009/130481 discloses pyrrole compounds that may be used in the prevention or treatment of fungal disease.

SUMMARY OF THE INVENTION

The present inventors have found that the pyrrole compound 2-(1,5-dimethyl-3-phenyl-1H-pyrrol-2-yl)-N-(4-(4-(5-fluoropyrimidin-2-yl)piperazin-1-yl)phenyl)-2-oxoacetamide (the compound of Formula I) is a particularly effective antifungal agent. It shows high potency in enzyme inhibition and fungal inhibition tests and has good bioavailability and low toxicity. Tests have shown that this pyrrole compound inhibits the growth of a wide variety of fungi, in particular the human pathogenic fungi *Aspergillus*. This particular compound has been shown to have activity against a wider spectrum of species within the *Aspergillus* genus than other pyrrole compounds. Further, the compound has been shown to exhibit increased in vivo efficacy when compared to the known antifungal drug Voriconazole, in particular improved efficacy against *Scedosporium* fungi. The compound 2-(1,5-dimethyl-3-phenyl-1H-pyrrol-2-yl)-N-(4-(4-(5-fluoropyrimidin-2-yl)piperazin-1-yl)phenyl)-2-oxoacetamide may, therefore, be used to effectively treat a wide variety of fungal infection and disease. These results are described in the international patent application having application number PCT/GB2015/053546, the entirety of which is incorporated by reference herein.

The present inventors have recognised a need for effective formulations of the pyrrole compound 2-(1,5-dimethyl-3-phenyl-1H-pyrrol-2-yl)-N-(4-(4-(5-fluoropyrimidin-2-yl) piperazin-1-yl)phenyl)-2-oxoacetamide. Formulations yielding high bioavailability with minimal side-effects are required for the compound to achieve optimal benefit in clinical use. There is further a need for formulations of 2-(1,5-dimethyl-3-phenyl-1H-pyrrol-2-yl)-N-(4-(4-(5-fluoropyrimidin-2-yl)piperazin-1-yl)phenyl)-2-oxoacetamide which can be easily administered to a patient in need thereof.

Accordingly, the present invention provides a pharmaceutical composition suitable for oral administration wherein the composition comprises spray-dried particles of a compound of Formula I or a pharmaceutically acceptable salt thereof

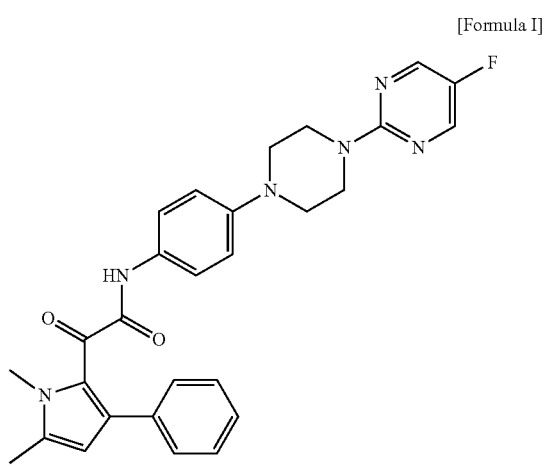 [SMILES: Cc1cc(-c2ccccc2)c(C(=O)C(=O)Nc2ccc(N3CCN(c4ncc(F)cn4)CC3)cc2)n1C]

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide.

In one aspect, the composition suitable for oral administration comprises spray-dried particles of the compound of Formula I. In one aspect, the compound of Formula I is substantially amorphous. In one aspect the pharmaceutical composition further comprises one or more excipients. In one aspect the composition comprises the excipient hydroxypropyl methyl cellulose acetate succinate (HPMCAS). In one aspect, the mass ratio of the compound of Formula I to excipient is from 1:100 to 1:1, for example from 1:15 to 1:2. In one aspect, the pharmaceutical composition comprises particles which are obtainable by spray-drying from a solution comprising an organic solvent selected from dichloromethane, methanol, and mixtures thereof. In one aspect, the pharmaceutical composition is in the form of a solid oral dosage form or a liquid oral dosage form. In one aspect, the liquid oral dosage form further comprises a pharmaceutically acceptable buffer having a pKa in the range 6.0 to 8.0. In one aspect, the buffer is from 1 mM to 200 mM phosphate buffer wherein the composition is buffered to about pH 7. In one aspect, the pharmaceutical further comprises one or more pharmaceutically acceptable binders and/or carriers and/or excipients and/or diluents and/or adjuvants.

The present invention also provides a pharmaceutical composition suitable for parenteral administration comprising (i) a compound of Formula I or a pharmaceutically acceptable salt thereof, (ii) a cyclodextrin or modified cyclodextrin, and (iii) a polyethylene glycol.

In one aspect, the composition suitable for parenteral administration comprises from 10 wt % to 40 wt % of a cyclodextrin or modified cyclodextrin; and/or from 10 wt % to 40 wt % of a polyethylene glycol. In one aspect, the cyclodextrin or modified cyclodextrin is hydroxy propyl beta cyclodextrin. In one aspect, the polyethylene glycol is PEG300 or PEG400. In one aspect, the composition further comprises polyvinyl pyrrolidone (Povidone). In one aspect, the compound of Formula I or the pharmaceutically acceptable salt thereof is present at a concentration of from 1 mg/mL to 10 mg/mL. In one aspect, the composition further comprises one or more pharmaceutically acceptable carriers and/or excipients and/or diluents and/or adjuvants.

The present invention also provides a pharmaceutical composition as described herein for use in a method of treatment of a human or animal subject in need thereof, particularly in a method of preventing or treating fungal infection in the subject. Similarly, the present invention provides a method of preventing or treating fungal infection in a human or animal subject in need thereof, said method comprising administering to the human or animal subject a therapeutically effective amount of a pharmaceutical composition as described herein; and the use of a pharmaceutical composition as described herein in the manufacture of a medicament for use in the prevention or treatment of fungal infection in a human or animal subject in need thereof.

The invention further provides a method of producing a pharmaceutical composition comprising a compound of Formula I or a pharmaceutically acceptable salt thereof, wherein said method comprises spray-drying a solution of the compound of Formula (I) or salt thereof. In one aspect, the method comprises: (i) dissolving one or more excipients in a solvent; (ii) adding the compound of Formula I to the solution produced in step (i); and (iii) spray drying the solution produced in step (ii).

The invention further provides a pharmaceutical composition suitable for oral administration wherein the composition comprises substantially amorphous particles of a compound of Formula I or a pharmaceutically acceptable salt thereof.

The compositions of the invention are beneficial as they provide extremely high bioavailability of the compound of Formula I and have minimal side-effects.

DETAILED DESCRIPTION OF THE INVENTION

Figure 1:
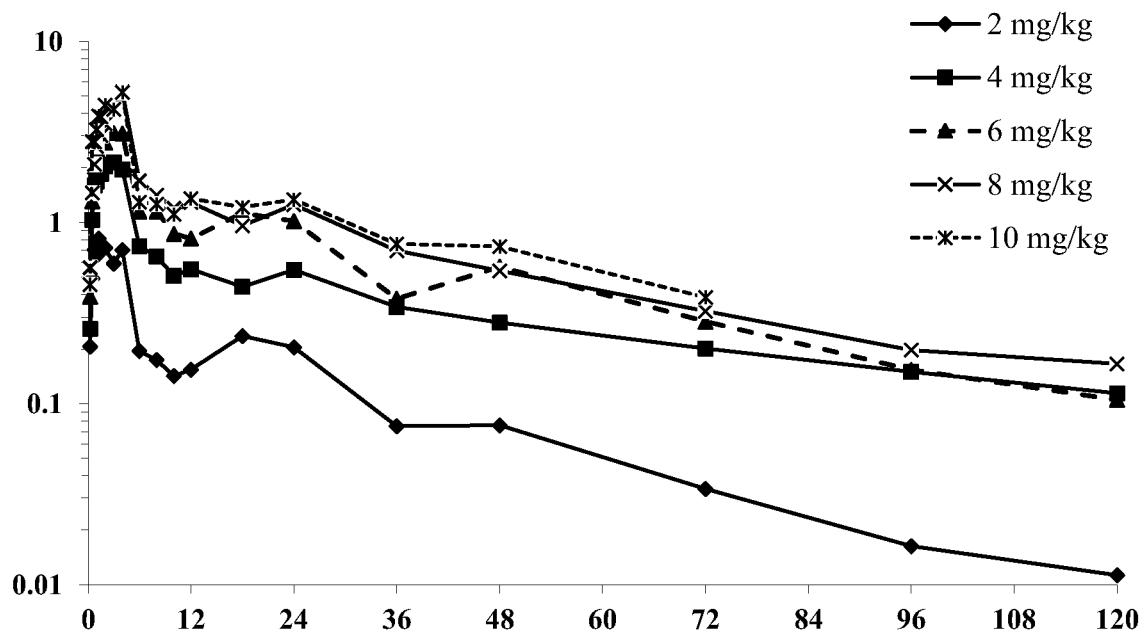
FIG. 1 shows pharmacokinetic data obtained in human trials of a formulation of the compound of Formula I according to the invention as described in Example 5. y-axis: Plasma $C_{max}$ (µg/mL); x-axis: time in hours.

As used herein, a pharmaceutically acceptable salt is a salt with a pharmaceutically acceptable acid or base. Pharmaceutically acceptable acids include both inorganic acids for example hydrochloric, sulphuric, phosphoric, diphosphoric, hydrobromic, hydroiodic or nitric acid and organic acids for example citric, fumaric, maleic, malic, ascorbic, succinic, tartaric, benzoic, acetic, methanesulphonic, ethanesulphonic, benzenesulphonic, p-toluenesulphonic acid, formic, acetic, propionic, glycolic, lactic, pyruvic, oxalic, salicylic, trichloroacetic, picric, trifluoroacetic, cinnamic, pamoic, malonic, mandelic, bismethylene salicylic, ethanedisulfonic, gluconic, citraconic, aspartic, stearic, palmitic, EDTA, p-aminobenzoic or glutamic acid, sulfates, nitrates, phosphates, perchlorates, borates, acetates, benzoates, hydroxynaphthoates, glycerophosphates or ketoglutarates. Further examples of pharmaceutically acceptable inorganic or organic acid addition salts include the pharmaceutically acceptable salts listed in Journal of Pharmaceutical Science, 66, 2 (1977) which are known to the skilled artisan. Pharmaceutically acceptable bases include alkali metal (e.g. sodium or potassium) and alkali earth metal (e.g. calcium or magnesium) hydroxides and organic bases for example alkyl amines, aralkyl amines and heterocyclic amines, lysine, guanidine, diethanolamine and choline. Also intended as pharmaceutically acceptable acid addition salts are the hydrates which the present compound is able to form. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compound of the active substance may form solvates with standard low molecular weight solvents using methods known to the skilled artisan.

Unless otherwise stated, all percentages mentioned herein are weight percentages (wt %).

The invention provides a pharmaceutical composition suitable for oral administration wherein the composition comprises spray-dried particles of a compound of Formula I or a pharmaceutically acceptable salt thereof

[Formula I]

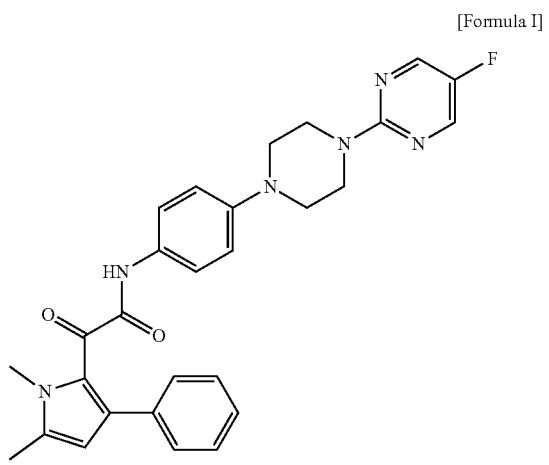 [SMILES: Cc1cc(-c2ccccc2)c(C(=O)C(=O)Nc2ccc(N3CCN(c4ncc(F)cn4)CC3)cc2)n1C]

2-(1,5-dimethyl-3-phenyl-1H-pyrrol-2-yl)-N-(4-(4-(5-fluoropyrimidin-2-yl)piperazin-1-yl)phenyl)-2-oxoacetamide Preferably, the composition comprises spray-dried particles of the compound of Formula I. Most preferably the composition comprises the compound of Formula I in the form of the free base.

Spray drying is a well-known technique used to produce substantially amorphous particles of substances for example pharmaceutically active substances e.g. drugs. Spray drying is particularly beneficial for producing solid particles of thermally-sensitive materials and has the advantage over other drying techniques that a broadly consistent particle size is obtained. Any suitable spray drying apparatus can be used to dry the substance, and many spray-dryers are commercially available. For example, the spray-dryer may be a single effect spray dryer or a multiple effect spray dryer. Multiple effect spray dryers are often preferred as they can be used to produce uniform particle sizes. Spray drying is described in standard reference texts which are readily available to the skilled person, for example A. S. Mujumdar, *Handbook of Industrial Drying*, CRC Press 2014, which describes spray-drying techniques and optimal choices thereof.

Preferably, the pharmaceutical composition suitable for oral administration comprises a compound of Formula I which is substantially amorphous. An amorphous particle is a particle which lacks long-range crystallographic ordering. Preferably, the compound of Formula 1 is more than 50% amorphous, for example more than 70% amorphous, more preferably more than 90% amorphous, still more preferably more than 95% amorphous, more preferably more than 99% amorphous, for example more than 99.5% amorphous or more than 99.9% amorphous. Substantially amorphous particles are therefore particles in which the compound of Formula I has a low crystallinity content, for example less than 50% crystallinity, e.g. less than 30% crystallinity, preferably less than 10%, especially less than 5% e.g. less than 1% crystallinity, for example less than 0.5% or less than 0.1% crystallinity. Crystallinity may be measured using methods familiar to those skilled in the art. There are many methods of testing amorphous particles which are known to the skilled person and which can be used to determine whether a particle is amorphous or crystalline. These methods include, but are not limited to powder X-ray diffraction, differential scanning calorimetry, dynamic vapour sorption, isothermal microcalorimetry, inverse gas chromatography, near infra-red spectroscopy and solid-state NMR.

Preferably, the pharmaceutical composition suitable for oral administration comprises particles of the compound of Formula I which have an average particle size of from about 0.5 μm to about 1000 μm, more preferably from about 1 μm to about 500 μm for example from 5 μm to 100 μm, for example from about 20 μm to about 50 μm. The term "average particle size" refers to the value known as the D50. The term D50 means that 50 vol % of the particles have a diameter that is smaller than this value, and 50 vol % of the particles have a diameter that is larger than this value. The average particle size may be measured using standard laser diffraction particle sizing techniques known in the art. One example of an instrument to measure the particle size of the dry powders is the Mastersizer 2000, manufactured by Malvern Instruments Ltd (Worcestershire, UK).

Preferably, the pharmaceutical composition suitable for oral administration comprises particles which are obtainable by spray-drying from a solution comprising an organic solvent. Preferably, the organic solvent is one or more solvents selected from dicholoromethane, acetone, methanol and ethanol. More preferably, the solvent is a mixture of two or more solvents selected from dicholoromethane, acetone, methanol and ethanol. Still more preferably, the solvent is a mixture of dichloromethane and/or acetone with methanol and/or ethanol. Typically, the ratio of dicholoromethane and/or acetone to methanol and/or ethanol is from 1:1 to 5:1, for example from 2:1 to 4:1 e.g. 3:1. For example, the solvent is often a mixture of dicholoromethane and methanol, wherein the ratio of dicholoromethane to methanol is from 2:1 to 4:1 for example 3:1. Most preferably, the solvent is a 3:1 ratio of dicholoromethane to methanol. Ratios of solvents can be determined by mass or volume; volume ratios are preferred.

Preferably, the pharmaceutical composition suitable for oral administration further comprises one or more excipients. Pharmaceutically acceptable excipients known to the skilled person include e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

More preferably, the pharmaceutical composition suitable for oral administration comprises an excipient selected from (i) a cellulose or modified cellulose for example hypromellose, hydroxypropyl cellulose, hydroxyl propyl methyl cellulose (HPMC), hydroxyl propyl methyl cellulose acetate (HPMCA) and hydroxy propyl methyl cellulose acetate succinate (HPMCAS) and (ii) a vinylpyrrolidone—vinyl acetate copolymer having a mass ratio of vinylpyrrolidone to vinyl acetate in the copolymer of from 10:1 to 1:10, for example from 5:1 to 1:5 e.g. 3:1 to 1:1, for example from 2:1 to 1:1, e.g. 3:2 (which can also be expressed as 6:4), for example Kollidon VA64 or Kollidon VA64 Fine, both available from BASF; Kollidon VA64 is preferred. The pharmaceutical composition may comprise a mixture of (i) and (ii). More preferably, the pharmaceutical composition suitable for oral administration comprises a cellulose-based excipient according to option (i). Most preferable excipients include HPMC, HPMCA and HPMCAS; HPMCAS is still more preferred.

HPMCAS is hydroxypropyl methyl cellulose acetate succinate. The content of acetyl and succinoyl groups in the polymer can determine the properties of the HPMCAS. Type L HPMCAS represents polymers with high ratio of succinoyl substitution to acetyl substitution; typically 14-18 wt % succinoyl content and 5-9 wt % acetyl content. Type M HPMCAS represents polymers having a lower ratio; typically 10-14 wt % succinoyl content and 7-11 wt % acetyl content. Type H HPMCAS typically comprises 4-8 wt % HPMCAS succinoyl content and 10-14 wt % acetyl content. Type L HPMCAS usually dissolves at around pH≥5.5; type M HPMCAS typically dissolves around pH≥6.0 and type H HPMCAS typically dissolves around pH≥6.8. Usually, the HPMCAS comprises from 12-28 wt % methoxyl and from 4-28% hydroxypropoxy. HPMCAS is readily available commercially from suppliers such as Shin-Etsu (product AQOAT) and from Ashland ("AquaSolve"). Any suitable HPMCAS known to those skilled in the art can be used.

Preferably, when an excipient is present in the pharmaceutical composition suitable for oral administration, the mass ratio of the compound of Formula I to the excipient is from 1:100 to 1:1. More preferably, the mass ratio of the compound of Formula 1 to the excipient is from 1:50 to 1:1, for example from 1:25 to 1:1.5 e.g. from 1:15 to 1:2, for example 1:10, 1:7, 1:5, 1:4 or 1:3. Most preferably the mass ratio of the compound of Formula 1 to the excipient is from 1:9 to 1:11, for example 1:10, or is from 1:3 to 1:5, for example 1:4. A mass ratio of the compound of Formula 1 to the excipient of 1:4 can be achieved by, for example, a mass ratio of the compound of Formula 1 to the excipient of 4:16.

The pharmaceutical composition of the invention suitable for oral administration typically contains from 1 to 50 wt % of the compound of Formula I; more typically from 4 to 40 wt % for example from 7 to 30 wt %. For example, the pharmaceutical composition may comprise from 5 to 20 wt %, for example from 8 to 15 wt %, e.g. from 9 to 11 wt % e.g. 10 wt %. A composition comprising about 10 wt % of the compound of Formula I can, for example, be produced using a composition comprising only the compound of Formula I and an excipient for example HPMCAS by using a weight ratio of 1:9 (compound of Formula I: HPMCAS). Alternatively, the pharmaceutical composition may comprise from 10 to 40 wt % of the compound of Formula I, for example from 15 to 30 wt % e.g. from 18 to 22 wt % for example about 20 wt %. A composition comprising 20 wt % of the compound of Formula I can, for example, be produced using a composition comprising only the compound of Formula I and an excipient for example HPMCAS by using a weight ratio of 4:16 (compound of Formula I: HPMCAS).

The pharmaceutical composition suitable for oral administration may further comprise one or more pharmaceutically acceptable binders and/or carriers and/or excipients (i.e. further to excipient(s) above) and/or diluents and/or adjuvants.

The pharmaceutical composition suitable for oral administration may preferably be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc. Preferably, the pharmaceutical composition suitable for oral administration is in the form of (i) a solid oral dosage form or (ii) a liquid oral dosage form. More preferably, the pharmaceutical composition suitable for oral administration is in the form of a solid oral dosage form.

Solid oral dosage forms include, for example, tablets and capsules. Solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, e.g. lecithin, polysorbates, laurylsulphates; and, in general, non-toxic and pharmacologically inactive substances used in pharmaceutical formulations. Such pharmaceutical preparations may be manufactured in any known manner, for example, by means of mixing, granulating, tabletting, sugar-coating, or film coating processes.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other solid oral dosage forms include lozenges comprising the active agent in a flavoured base, usually sucrose and acacia or tragacanth and pastilles comprising the active agent in an inert base such as gelatin and glycerin, or sucrose and acacia.

Liquid oral dosage forms include solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol. Liquid oral dosage forms include mouthwashes comprising the active agent in a suitable liquid carrier.

Preferably, when the pharmaceutical composition suitable for oral administration is in the form of a liquid oral dosage form, the liquid oral dosage form further comprises a pharmaceutically acceptable buffer having a pKa in the range 6.0 to 8.0, preferably around pH 7, for example from pH 6.5 to pH 7.5 e.g. from pH 7.0 to pH 7.5, preferably around pH 7.1 to pH 7.3 e.g. around pH 7.2. Any pharmaceutically acceptable buffer which is capable of maintaining the pH of the solution in this range can be used. For example, suitable buffer salts include citrate (e.g. sodium citrate/citric acid), phosphate (e.g. $Na_2HPO_4/NaH_2PO_4$) and carbonate (e.g. sodium carbonate/sodium bicarbonate). Phosphate buffer is preferred. The salt concentration of the buffer can be any suitable salt concentration to produce a desired liquid oral formulation. Generally, the salt concentration in the buffer solution is chosen to maintain the pH of the solution at the desired value, for example at around pH 7 (e.g. pH 7.2). Typical salt concentrations are from 1 mM to 200 mM, for example from 5 mM to 100 mM e.g. from 10 mM to 50 mM, for example from 20 mM to 40 mM, e.g. around 25 mM, around 30 mM, or around 35 mM.

Preferred compositions of the invention suitable for oral administration therefore comprise spray-dried particles of a compound of Formula I or a pharmaceutically acceptable salt thereof, wherein the compound of Formula I is substantially amorphous and wherein the composition further comprises one or more excipients.

More preferred compositions of the invention suitable for oral administration comprise spray-dried particles of a compound of Formula I, wherein the compound of Formula I is substantially amorphous and wherein the composition further comprises the excipient hydroxypropyl methyl cellulose acetate succinate (HPMCAS).

Still more preferred compositions of the invention suitable for oral administration comprise spray-dried particles of the compound of Formula I, wherein the compound of Formula I is substantially amorphous and wherein the composition further comprises the excipient HPMCAS, and wherein the mass ratio of the compound of Formula I to the excipient is from 1:100 to 1:1, preferably from 1:15 to 1:2.

Yet more preferred compositions of the invention suitable for oral administration comprise spray-dried particles of the compound of Formula I, wherein the compound of Formula I is substantially amorphous and is obtainable by spray-drying from a solution comprising an organic solvent selected from dichloromethane, methanol, and mixtures thereof, and wherein the composition further comprises the excipient HPMCAS, and wherein the mass ratio of the compound of Formula I to the excipient is from 1:15 to 1:2.

Most preferred compositions of the invention suitable for oral administration comprise spray-dried particles of the compound of Formula I, wherein the compound of Formula I is substantially amorphous, and wherein the composition comprises 10 wt % of the compound of Formula I and 90 wt % HPMCAS (i.e. the mass ratio of the compound of Formula I to HPMCAS is 1:9). The compound of formula I is most preferably obtainable by spray-drying from a 3:1 v/v mixture of dichloromethane:methanol.

Similarly, most preferred compositions of the invention suitable for oral administration comprise spray-dried particles of the compound of Formula I, wherein the compound of Formula I is substantially amorphous, and wherein the composition comprises 20 wt % of the compound of Formula I and 80 wt % HPMCAS (i.e. the mass ratio of the compound of Formula I to HPMCAS is 1:4). The compound of formula I is most preferably obtainable by spray-drying from a 3:1 v/v mixture of dichloromethane:methanol.

The invention also provides a pharmaceutical composition suitable for oral administration wherein the composition comprises substantially amorphous particles of a compound of Formula I or a pharmaceutically acceptable salt thereof. The composition is as described herein.

More preferably, the invention provides a pharmaceutical composition suitable for oral administration comprising the compound of Formula I wherein the compound of Formula I is substantially amorphous and the composition further comprises HPMCAS, wherein the mass ratio of the compound of Formula I to the HPMCAS is from about 1:3 to 1:5, for example 1:4, or from about 1:8 to 1:10, for example about 1:9. Therefore, the invention provides a pharmaceutical composition suitable for oral administration comprising the compound of Formula I and HPMCAS, wherein the compound of Formula I is substantially amorphous and the composition comprises 10 wt % of the compound of Formula I and 90 wt % HPMCAS. The invention also provides a pharmaceutical composition suitable for oral administration comprising the compound of Formula I and HPMCAS, wherein the compound of Formula I is substantially amorphous and the composition comprises 20 wt % of the compound of Formula I and 80 wt % HPMCAS.

The invention also provides a method of producing a pharmaceutical composition comprising a compound of Formula I or a pharmaceutically acceptable salt thereof

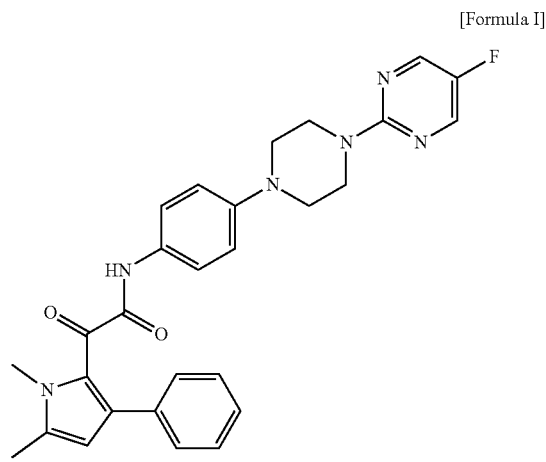 [SMILES: Cc1cc(-c2ccccc2)c(C(=O)C(=O)Nc2ccc(N3CCN(c4ncc(F)cn4)CC3)cc2)n1C]

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide wherein said method comprises spray-drying a solution of the compound of Formula (I) or salt thereof.

Any suitable spray-drying technique can be used. Spray-drying is described above.

Preferably, the method of producing a pharmaceutical composition suitable for oral administration comprises the steps of:
 i) dissolving one or more excipients in a solvent;
 ii) adding the compound of Formula I to the solution produced in step (i); and
 iii) spray drying the solution produced in step (ii).

Preferably, one or more of the one or more excipients is an excipient described herein. More preferably, the one or more excipients is (i) a cellulose or modified cellulose as described herein or (ii) a vinylpyrrolidone—vinyl acetate copolymer as described herein, or a mixture of (i) and (ii). Most preferably, the excipient is HPMCAS as described herein.

Preferably, the solvent is an organic solvent as described herein. More preferably, the solvent is a mixture of dichloromethane and/or acetone with methanol and/or ethanol. Still more preferably, the solvent is a mixture of dicholoromethane and methanol, wherein the ratio of dicholoromethane to methanol is from 2:1 to 4:1 for example 3:1. Most preferably, the solvent is a 3:1 ratio of dicholoromethane to methanol.

For example, the invention therefore provides a method of producing a pharmaceutical composition suitable for oral administration as described herein wherein:
the excipient is hydroxypropyl methyl cellulose acetate succinate (HPMCAS);
the solvent is a mixture of dichloromethane and methanol, wherein the volume ratio of dichloromethane to methanol is from 5:1 to 1:1;
the concentration of the excipient in the solvent is from 5% to 20% w/v; and
the compound of Formula I is added to the solution of the excipient in the solvent to give a concentration of 0.5% to 10% by mass.
More preferably, the invention provides a method of producing a pharmaceutical composition suitable for oral administration as described herein wherein:
the excipient is hydroxypropyl methyl cellulose acetate succinate (HPMCAS);
the solvent is a mixture of dichloromethane and methanol, wherein the volume ratio of dichloromethane to methanol is from 4:1 to 2:1;
the concentration of the excipient in the solvent is from 7% to 18% w/v; and
the compound of Formula I is added to the solution of the excipient in the solvent to give a concentration of 0.5% to 6% by mass.
Still more preferably, the invention provides a method of producing a pharmaceutical composition suitable for oral administration as described herein wherein:
the excipient is hydroxypropyl methyl cellulose acetate succinate (HPMCAS);
the solvent is a mixture of dichloromethane and methanol, wherein the volume ratio of dichloromethane to methanol is about 3:1; and
(i) the concentration of the excipient in the solvent is from about 7 wt % to about 11 wt %; and the compound of Formula I is added to the solution of the excipient in the solvent to give a concentration of about 0.5% to about 2% by mass; or
(ii) the concentration of the excipient in the solvent is from about 12% to about 18%; and the compound of Formula I is added to the solution of the excipient in the solvent to give a concentration of about 3% to about 5% by mass
Most preferably, the invention provides a method of pharmaceutical composition suitable for oral administration comprising
i) dissolving from about 7 wt % to about 11 wt % (e.g. about 9 wt %) of HPMCAS in a solvent wherein the solvent is a 3:1 v/v mixture of dichloromethane:methanol;
ii) adding the compound of Formula I to the solution produced in step (i) to yield a solution wherein the concentration of the compound of Formula I is about 0.5% to about 2% by mass (e.g. about 1% by mass); and
iii) spray drying the solution produced in step (ii).
Similarly, the invention provides a method of pharmaceutical composition suitable for oral administration comprising i) dissolving from about 12 wt % to about 18 wt % (e.g. about 16 wt %) of HPMCAS in a solvent wherein the solvent is a 3:1 v/v mixture of dichloromethane:methanol;
ii) adding the compound of Formula I to the solution produced in step (i) to yield a solution wherein the concentration of the compound of Formula I is about 3% to about 5% by mass (e.g. about 4% by mass); and
iii) spray drying the solution produced in step (ii).

The invention also provides a pharmaceutical composition suitable for parenteral administration comprising (i) a compound of Formula I or a pharmaceutically acceptable salt thereof,

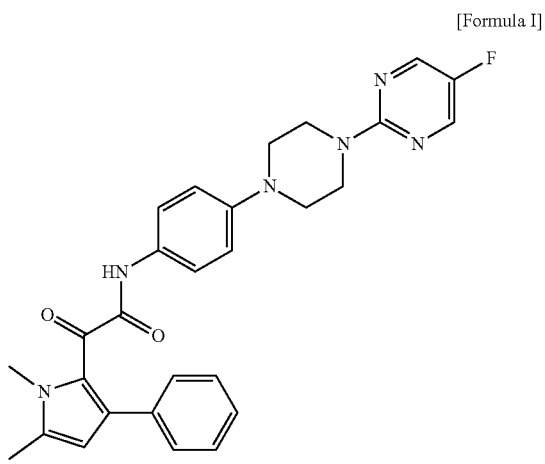 [SMILES: Cc1cc(-c2ccccc2)c(C(=O)C(=O)Nc2ccc(N3CCN(c4ncc(F)cn4)CC3)cc2)n1C]

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide (ii) cyclodextrin or modified cyclodextrin, and (iii) polyethylene glycol.

Pharmaceutically acceptable salts are described herein. Preferably, the pharmaceutical composition suitable for parenteral administration comprises a compound of Formula I. More preferably, the pharmaceutical composition suitable for parenteral administration comprises a compound of Formula I in the form of the free base.

Preferably, cyclodextrin is present in an amount of from 10 wt % to 40 wt % with reference to the pharmaceutical composition. Typical amounts of cyclodextrin present in the composition are from 20 wt % to 30 wt % for example about 25 wt %.

Preferably, polyethylene glycol is present in an amount of from 10 wt % to 40 wt % with reference to the pharmaceutical composition. Typical amounts of polyethylene glycol present in the composition are from 20 wt % to 30 wt % for example about 25 wt %.

The pharmaceutical composition suitable for parenteral administration may comprise any suitable cyclodextrin or mixture thereof. Typical cyclodextrins contain a number of glucose monomers ranging from six to eight units in a ring, creating a cone shape. Cyclodextrins are often denoted as α (alpha)-cyclodextrin (comprising a 6-membered sugar ring molecule); β (beta)-cyclodextrin (comprising a 7-membered sugar ring molecule) or γ (gamma)-cyclodextrin (comprising an 8-membered sugar ring molecule). Because cyclodextrins are hydrophobic inside and hydrophilic outside, they can form complexes with hydrophobic compounds. Thus they can enhance the solubility and bioavailability of such compounds. Alpha-, beta-, and gamma-cyclodextrin are all generally recognized as safe by the FDA. Cyclodextrins (CDs) can be modified in various ways whilst still be suitable for use in the compositions of the invention. For example, known modified cyclodextrins include Hydroxyethyl-β-CD (HE-β-CD), Hydroxypropyl-β-CD (HP-β-CD), Sulfobutylether-β-CD (SBE-β-CD), Methyl-β-CD (M-β-CD), Dimethyl-β-CD (DM-β-CD/DIMEB), Randomly dimethylated-β-CD (RDM-β-CD), Randomly methylated-β-CD (RM-β-CD/RAMEB), Carboxymethyl-β-CD (CM-β-CD), Carboxymethyl ethyl-β-CD (CME-β-CD), Diethyl-β-CD (DE-β-CD), Tri-O-methyl-β-CD (TRIMEB), Tri-O-ethyl-β-CD (TE-β-CD), Tri-O-butyryl-β-CD (TB-β-CD), Tri-O-valeryl-β-CD (TV-β-CD), Di-O-hexanoyl-β-CD (DH-β-CD), Glucosyl-β-CD G1-β-CD Maltosyl-β-CD (G2-β-CD), and 2-hydroxy-3-trimethyl-ammoniopropyl-β-CD (HT-MAPCD). Cyclodextrins and their uses in pharmaceutical formulations are disclosed in standard reference texts, for example Frömming and Szejtli, *Cyclodextrins in Pharmacy*, Springer, 1993, which describes the advantages of specific cyclodextrins in pharmaceutical formulations.

Preferably, the cyclodextrin is selected from hydroxy propyl beta cyclodextrin and sulfobutyl ether beta-cyclodextrin (Captisol) and mixtures thereof. Hydroxy propyl beta cyclodextrin is preferred.

The pharmaceutical composition suitable for parenteral administration may comprise any suitable polyethylene glycol or mixture thereof. For example, the composition may comprise any polyethylene glycol approved for intraveneous use. Polyethylene glycols which can be used include PEG200-PEG500, for example PEG300 and/or PEG400. PEG 300 and PEG 400 are preferred, and PEG400 is most preferred.

As the skilled person will appreciate, the number following the term "PEG" (e.g. 300 in "PEG300") refers to the average molecular weights of the PEG molecule. PEG400 thus typically comprises approximately 9 ethylene glycol units in each polymer molecule, and PEG 300 typically comprises 7 ethylene glycol units in each polymer molecule. However, as the skilled person will appreciate, many commercially available PEGs are polydisperse. In general terms, the molecular weight distribution can be characterized statistically in terms of its weight average molecular weight (Mw) and its number average molecular weight (Mn), the ratio of which is often referred to as the polydispersity index (Mw/Mn). Both Mw and Mn can be measured by conventional techniques, for example, by mass spectrometry.

Preferably, the pharmaceutical composition suitable for parenteral administration comprises one or more dispersing agents for example low molecular weight povidone (polyvinyl pyrrolidone). Preferably, the povidone is endotoxin-free. Povidones are available from commercial suppliers for example Ashland (Plasdone). Preferably the povidone has a K-value of from 5 to 20 for example from 10 to 18. For example, the Povidone may have a nominal molecular weight of about 4000 and a K value of from about 10 to about 14. Alternatively the povidone may have a nominal molecular weight of about 10000 and a K value of from about 15 to about 18. The K value is a function of the average degree of polymerisation and the intrinsic viscosity of the polymer and can be calculated from the kinematic viscositiy of an aqueous solution of the polymer. Preferably, the povidone has a $T_g$ (glass transition temperature) of from about 110° C. to about 130° C. e.g. from about 120° C. to about 126° C. The pharmaceutical composition may comprise a mixture of two or more povidones.

Preferably, when the pharmaceutical composition suitable for parenteral administration comprises a povidone or mixture thereof, the povidone or mixture thereof is present in an amount of from 0.1 to 5 wt %, more preferably from 0.5 to 2 wt %, still more preferably about 1 wt % relative to the total mass of the composition.

Preferably, the compound of Formula I is present in the pharmaceutical composition suitable for parenteral administration at a concentration of from 1 mg/mL to 10 mg/mL. More preferably the concentration of the compound of Formula I in the pharmaceutical composition suitable for parenteral administration is from 2 to 7 mg/mL for example from 3 to 5 mg/mL e.g. 4 mg/mL.

The pharmaceutical composition suitable for parenteral administration may further comprise one or more pharmaceutically acceptable carriers and/or excipients and/or diluents and/or adjuvants. For example, the composition may contain as carrier, for example, sterile water, or may be in the form of a sterile, aqueous, isotonic saline solutions.

Preferably, the pharmaceutical composition suitable for parenteral administration is adjusted to a final pH of from about pH 4 to about pH 8.

More preferably, the pharmaceutical composition suitable for parenteral administration is adjusted to a final pH of from about pH 4 to about pH 6, for example from about pH 4.5 to about pH 5.5, e.g. about pH 5, for example pH 5.0. The pH of the pharmaceutical composition may be adjusted using any pharmaceutically acceptable acid or base. Phosphoric acid is preferred.

Preferred pharmaceutical compositions are sterile and pyrogen free.

Preferred compositions of the invention suitable for parenteral administration therefore comprise:
  from 10 wt % to 40 wt % cyclodextrin or modified cyclodextrin;
  from 10 wt % to 40 wt % polyethylene glycol; and
  a dispersing agent for example povidone.
For example, compositions of the invention suitable for parenteral administration may comprise:
  from 1 to 10 mg/mL of the compound of Formula I or a pharmaceutically acceptable salt thereof;
  from 10 wt % to 40 wt % hydroxyl propyl beta cyclodextrin;
  from 10 wt % to 40 wt % PEG300 or PEG400; and
  a dispersing agent for example povidone, wherein the povidone is as described herein; and
wherein the pH of the composition is adjusted to from about pH 4 to about pH 8.
More preferred compositions of the invention suitable for parenteral administration comprise:
  from 1 to 10 mg/mL of the compound of Formula I or a pharmaceutically acceptable salt thereof;
  from 10 wt % to 40 wt % hydroxyl propyl beta cyclodextrin;
  from 10 wt % to 40 wt % PEG300 or PEG400; and
  a dispersing agent for example povidone, wherein the povidone is as described herein; and
wherein the pH of the composition is adjusted to from about pH 4 to about pH 6.
Still more preferred compositions of the invention suitable for parenteral administration comprise:
  from 3 to 5 mg/mL of the compound of Formula I;
  from 20 wt % to 30 wt % hydroxyl propyl beta cyclodextrin;
  from 20 wt % to 30 wt % PEG300 or PEG400, preferably PEG400; and
  from 0.1 to 5 wt % povidone; and wherein the pH of the composition is adjusted to from about pH 4.5 to about pH 5.5.

Most preferred compositions of the invention suitable for parenteral administration comprise:
- 4 mg/mL (relative to the final volume of the composition) of the compound of Formula I
- 25 wt % hydroxy propyl beta cyclodextrin;
- 25 wt % PEG400;
- 1 wt % polyvinyl pyrrolidone (Povidone);
- phosphoric acid in sufficient amount to adjust the pH of the pharmaceutical composition to pH 5.0; and
- water to 100%.

As described herein, a pharmaceutical composition of the invention can further comprise one or more adjuvants for example a local anaesthetic, preservative or buffering agent.

Pharmaceutically acceptable binders include solution binders and dry binders. Solution binders are dissolved in a solvent (for example water or alcohol can be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

Pharmaceutical carriers include liposomes, nanospheres, micelles, protein-DNA complexes, nanogels and natural solvents for example aqueous and non-aqueous solutions.

Other substances useful as excipients, diluents or carriers include acacia, alginate, alginic acid, aluminum acetate, benzyl alcohol, butyl paraben, butylated hydroxy toluene, citric acid, calcium carbonate, candelilla wax, croscarmellose sodium, confectioner's sugar, colloidal silicone dioxide, cellulose, calcium phosphate, carnuba wax, corn starch, carboxymethylcellulose calcium, calcium stearate, calcium disodium EDTA, copolyvidone, hydrogenated castor oil, calcium hydrogen phosphate dehydrate, cetylpyridine chloride, cysteine HCl, crosspovidone, disodium hydrogen phosphate, dimethicone, sodium erythrosine, ethyl cellulose, gelatin, glyceryl monooleate, glycerine, glycine, glyceryl monostearate, glyceryl behenate, hydroxy propyl cellulose, hydroxyl propyl methyl cellulose, hypromellose, HPMC pthalate, lactose, magnesium stearate, mannitol, methyl cellulose, magnesium carbonate, mineral oil, magnesium oxide, methyl paraben, povidone, polysorbate 80, polyethylene oxide, polaxamer 407 or 188, potassium bicarbonate, potassium sorbate, potato starch, phosphoric acid, polyoxy stearate, sodium starch glycolate, sodium crossmellose, sodium lauryl sulphate, starch, silicon dioxide, sodium benzoate, stearic acid, sucrose, sorbic acid, sodium carbonate, saccharin sodium, sodium alginate, silica gel, sorbiton monooleate, sodium stearyl fumarate, sodium chloride, sodium metabisulfite, sodium citrate dehydrate, sodium carboxy methyl cellulose, succinic acid, sodium propionate, titanium dioxide, talc, triacetin and triethyl citrate.

A pharmaceutical composition as described herein may comprise particles of the compound of Formula I wherein the average particle size (as described herein) has undergone particle size reduction by micronisation or nanonisation technologies.

The compositions of the invention are particularly advantageous as they provide the compound of Formula I with increased bioavailability. As used herein, bioavailability is defined such that a drug for example the compound of Formula I, when administered intraveneously, has a bioavailability of 100%. The pharmaceutical compositions of the invention which are suitable for oral administration are particularly beneficial as they can provide the compound of Formula I with high bioavailability. Preferably, the composition of the invention provides the compound of Formula I with a bioavailability of at least 50%, more preferably at least 70% for example at least 80%, still more preferably at least 90% for example at least 95%. As the skilled person will appreciate, bioavailability can be determined by numerous factors including the nature of the subject to which the composition is administered (age, weight, sex etc). Therefore, a negative result in one subject group is not determinative.

Bioavailability can be determined by pharmacokinetic (PK) studies in which plasma drug concentration is determined as a funcation of time after both intravenous (IV) and extravascular (e.g., oral) administration. The absolute bioavailability ($F_{abs}$) is the dose (D)-corrected area under curve (AUC) (non-intravenous) divided by AUC (intravenous). As used herein, $F_{abs}$ for a drug administered by the oral route (PO) is calculated using:

$$F_{abs} = 100 \frac{AUC_{PO} \cdot D_{IV}}{AUC_{IV} \cdot D_{PO}}$$

The compositions of the invention are useful in treating medical conditions in a human or animal subject in need thereof.

Accordingly, the invention provides a pharmaceutical composition as described herein for use in a method of treatment of a human or animal subject in need thereof. Preferably, the invention provides a pharmaceutical composition as described herein for use in the treatment of a human or animal subject in need thereof, wherein the treatment comprises prevention of or treatment of fungal infection in the subject.

The invention also provides a method of preventing or treating fungal infection in a human or animal subject in need thereof, said method comprising administering to the human or animal subject a therapeutically effective amount of a pharmaceutical composition as described herein.

The invention also provides the use of a pharmaceutical composition as described herein in the manufacture of a medicament for use in the prevention or treatment of fungal infection in a human or animal subject in need thereof.

A pharmaceutical composition of the invention may be used in a method of treating a human or animal subject wherein the treatment comprises administration of the composition in combination with a further antifungal agent as described herein.

A therapeutically effective amount of a composition of the invention may be administered to a patient in need thereof. For example, the composition is typically administered in an amount such as to provide to the subject a daily dose of the compound of Formula I of up to 200 mg, e.g. up to 100 mg or up to 50 mg per kg of body weight, for example from 0.001 to 200 or 0.001 to 50 mg per kg of body weight, according to (for example) the age, weight and conditions of the subject to be treated, the type and severity of the disease and the frequency and route of administration. Preferably, daily dosage levels are up to 200 mg, e.g. up to 150 mg, up to 100 mg, up to 50 mg or up to 40 mg per kg of body weight. Daily dosage levels are for example at least 1 mg, at least 2 mg or at least 5 mg per kg of body weight. In one embodiment the daily dosage level is from 0.05 mg to 2 g, preferably from 0.1 mg to 10 mg. The appropriate dosage level can be readily determined by the skilled physician.

Where a composition of the invention is administered together with a second antifungal agent, the second antifungal agent is typically administered at or below the standard dose used for that drug. In this manner, known antifungal agents may be administered in lower doses than are currently used, resulting in a reduction in toxic effects.

The composition of the invention is useful in the treatment of or prevention of fungal disease. Preferably, the fungal disease comprises an infection by a fungus, for example an Ascomycete. Preferably, the fungal disease comprises an infection by an organism selected from the genera *Absidia; Acremonium; Alternaria; Aspergillus; Bipolaris; Blastomyces; Blumeria; Cladosporium; Coccidioides; Colletotrichium; Curvularia; Encephalitozoon; Epicoccum; Epidermophyton; Exophiala; Exserohilum; Fusarium; Histoplasma; Leptosphaeria; Microsporum; Mycosphaerella; Neurospora, Paecilomyces; Penicillium; Phytophthora; Plasmopara; Pneumocystis; Pyricularia; Pythium; Puccinia; Rhizoctonia; Rhizomucor; Scedosporium; Scopulariopsis; Trichophyton; Trichosporon*; and *Ustilago*.

Preferably, the fungal disease comprises an infection by an organism of the genus *Aspergillus, Scedosporium* or *Fusarium*, for instance, the fungal disease comprises an infection by an organism of the genus *Aspergillus* or *Scedosporium*, in particular *Aspergillus*. In one embodiment, the fungal disease comprises an infection by an organism of the genus *Aspergillus*. In another embodiment, the fungal disease comprises an infection by an organism of the genus *Scedosporium*.

Preferably, the fungal disease comprises an infection by an organism selected from the species *Absidia corymbifera; Acremonium* spp; *Alternaria alternata; Aspergillus flavus; Aspergillus fumigatus; Aspergillus nidulans; Aspergillus niger; Aspergillus parasiticus; Aspergillus terreus; Bipolaris* spp; *Blastomyces dermatitidis; Blumeria graminis; Cladosporium cladosporoides; Cladosporium herbarium; Coccidioides immitis; Coccidioides posadasii; Curvularia lunata; Colletotrichium trifolii; Encephalitozoon cuniculi; Epicoccum nigrum; Epidermophyton floccosum; Exophiala* spp; *Exserohilum rostratum; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Penicillium chrysogenum; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Rhizomucor* spp; *Rhizopus* spp; *Scedosporium apiospermum; Scedosporium prolificans; Scedosporium* species d *Scopulariopsis brevicaulis; Trichophyton mentagrophytes; Trichophyton interdigitale; Trichophyton rubrum; Trichosporon asahii; Trichosporon beigelii*; and *Ustilago maydis*.

Preferably, the fungal disease comprises an infection by *A. fumigatus, A. flavus, A. terreus, A. niger, A. lentulus, S. apiospermum, S. prolificans*, or *S.* species *d*. Particularly, the fungal disease comprises an infection by *A. fumigatus, A. flavus, A. terreus* or *A. niger*. In one embodiment, the fungal disease comprises an infection by *S. prolificans*.

Examples of fungal diseases which can be prevented or treated using a composition of the invention include both systemic and superficial infections. The fungal diseases include invasive fungal diseases caused by *Aspergillus* species for example aspergillosis, but also local forms of these infections. For instance, the fungal diseases include invasive fungal diseases caused by *Aspergillus* species for example aspergillosis, but also local forms of these infections. Compositions of the invention is particularly useful against diseases caused by *Aspergillus* species, for which a fungicidal drug is required which has lower toxicity than amphotericin. The invention also provides for the treatment of dermatological infections.

The pharmaceutical composition of the invention is, in one embodiment, for use in the prevention or treatment of a disease caused by *Aspergillus* species. The diseases caused by *Aspergillus* species include diseases caused by *A. fumigatus, A. flavus, A. terreus* and *A. niger*.

Examples of systemic infections which might be prevented or treated using a pharmaceutical composition of the invention include: pulmonary aspergillosis, e.g. in immunosuppressed patients for example bone marrow recipients or AIDS patients; systemic aspergillosis; rhinocerebral mucomycosis; blastomycosis; histoplasmosis; coccidiomycosis; paracoccidiomycosis; lobomycosis; sporotrichosis; chromoblastomycosis; phaeohyphomycosis; and disseminated sporotrichosis.

Examples of superficial infections, which can be prevented or treated using a pharmaceutical composition of the invention include: ring worm; athlete's foot; and tinea unguium (nail infection).

Examples of diseases or conditions which are caused by fungi or where fungi exacerbate an allergic response, and which can be prevented or treated using a pharmaceutical composition of the invention include allergic bronchopulmonary aspergillosiis (ABPA); asthma, Severe asthma with Fungal Sensitisation (SAFS), fungal colonization of cystic fibrosis, rhinosinusitis and sinusitis. For instance, the disease may be caused by a fungal sensitisation, or the disease may be Allergic Bronchopulmonary Aspergillosis (ABPA) or asthma.

The pharmaceutical compositions described herein can be administered in combination with a second antifungal agent. Preferably, the pharmaceutical composition is administered separately from or successively with the second antifungal agent. For example, the composition of the invention and the second antifungal agent may be provided as a kit. The kit may thus comprise a composition of the invention and a second antifungal agent.

The second antifungal agent can be any suitable antifungal agent that the skilled person would judge to be useful in the circumstances. For example, any of the conditions described herein can be treated in his manner.

Particularly suitable classes of antifungal agents include azoles, polyenes, purine nucleotide inhibitors, pyrimidine nucleotide inhibitors, mannan inhibitors, protein elongation factor inhibitors, chitin synthase inhibitors, Beta-glucan synthase inhibitors, echinocandins, allylamines, anti-HSP90 antibodies, bactericidal/permeability inducing protein products and polyoxins. Other suitable antifungal agents which do not fall within the classes above include the compounds 5-fluoro-1,3-dihydro-1-hydroxy-2,1-benzoxaborale (AN269), 5-chloro-1,3-dihydro-1-hydroxy-2,1-benzoxaborale (AN2718) and icofungipen.

For instance, the second antifungal agent may be selected from the group consisting of azoles, polyenes, purine nucleotide inhibitors, pyrimidine nucleotide inhibitors, mannan inhibitors, protein elongation factor inhibitors, echinocandins, allylamines, anti-HSP90 antibodies, bactericidal/permeability inducing protein products or polyoxins, or one of the compounds 5-fluoro-1,3-dihydro-1-hydroxy-2,1-benzoxaborale (AN269), 5-chloro-1,3-dihydro-1-hydroxy-2,1-benzoxaborale (AN2718), icofungipen, VT116 or SCY078.

VT116 is 2-Pyridineethanol, α-(2,4-difluorophenyl)-β,β-difluoro-α-(1H-tetrazol-1-ylmethyl)-5-[4-(2,2,2-trifluoroethoxy)phenyl]-, (αR)-,

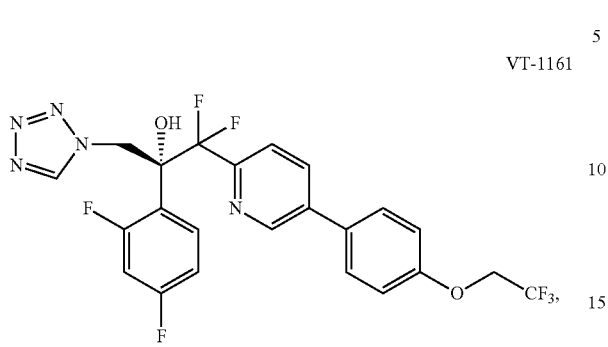

VT-1161 and SCY078 078 (aka MK-3118) is a semi-synthetic derivative of enfumafungin, 4H-1,4a-Propano-2H-phenanthro[1,2-c]pyran-7-carboxylic acid, 15-[(2R)-2-amino-2,3,3-trimethylbutoxy]-8-[(1R)-1,2-dimethylpropyl]-1,6,6a,7,8,9,10,10a,10b,11,12,12a-dodecahydro-1,6a,8,10a-tetramethyl-14-[5-(4-pyridinyl)-1H-1,2,4-triazol-1-yl]-, (1S,4aR,6aS,7R,8R,10aR,10bR,12aR,14R,15R):

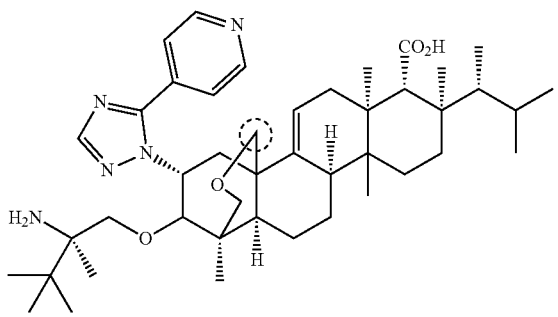

SCY-078

Preferred azoles are clotrimazole, econazole, bifonazole, butoconazole, fenticonazole, fluconazole, isoconazole, itraconazole, ketoconazole, miconazole, oxiconazole, sertaconazole, sulconazole, tioconazole, isavuconazole, ravuconazole, posaconazole, terconazole and voriconazole, luliconazole. Preferred echinocandins are anidulafungin, caspofungin micafungin and biafungin. Preferred allylamines are terbinafine, butenafine, amorolfine and naftifine. Preferred polyenes are amphotericin B and nystatin. A preferred example of a purine or pyrimidine nucleotide inhibitor is flucytosine. A preferred mannan inhibitor is pradamicin. A preferred protein elongation factor inhibitor is sordarin and analogues thereof. A preferred polyoxin is nikkomycin Z.

Particularly preferred second antifungal agents are caspofungin, micafungin, anidulofungin, amphotericin B, voriconazole, posaconazole, isavuconazole, fluconazole and itraconazole.

Synthesis

The compound of Formula I is 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof.

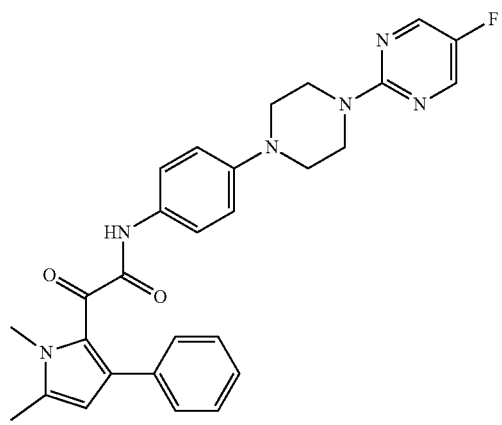

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide One synthetic route to the compound of Formula I is described herein. In general terms, the compound of Formula I may be synthesised by reacting a compound of formula (II), with a compound of formula (III). Typically the reaction takes place in the presence of an organic solvent and a base. Preferably the solvent is dichloromethane or tetrahydrofuran and the base is triethylamine or pyridine. Typically the reaction is carried out at 0° C. initially while the reagents are added and then stirred at room temperature until the reaction is complete. The compound of formula (III) is typically available from commercial sources or can be prepared by known methods.

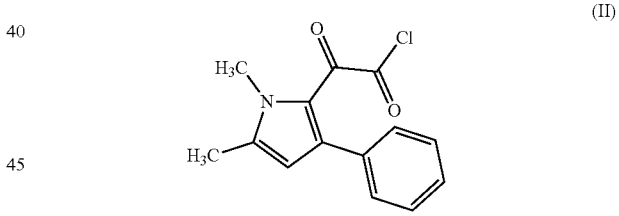

(II)

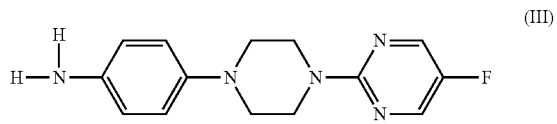

(III)

The compound of formula (II) may be prepared by reacting a compound of formula (IV), with preferably oxalyl chloride. Typically the reaction takes place in an organic solvent. Preferably, the solvent is dichloromethane. Typically, the reaction is carried out at 0° C. initially while the reagents are added and then stirred at room temperature until the reaction is complete.

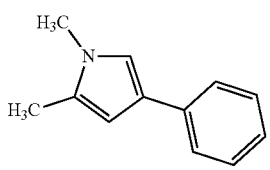

(IV)

All of the starting materials referred to in the reactions described above are available from commercial sources or can be prepared by analogy with known methods.

The following examples illustrate the invention but are not intended to limit the scope of the invention. In this regard, it is important to understand that the particular assays used in the Examples section are designed only to provide an indication of anti-fungal activity. There are many assays available to determine such activity, and a negative result in any one particular assay is therefore not determinative.

EXAMPLES

Example 1: Synthesis of the Compounds of Formula I (2-(1,5-dimethyl-3-phenyl-1H-pyrrol-2-yl)-N-(4-(4-(5-fluoropyrimidin-2-yl)piperazin-1-yl)phenyl)-2-oxoacetamide)

The synthesis of the compound of Formula I is described in the international patent application having application number PCT/GB2015/053546. Information relating to the synthesis of the compound of Formula I is incorporated by reference. The following Example is reproduced from that patent application.

The synthetic scheme below provides a method of synthesis of:

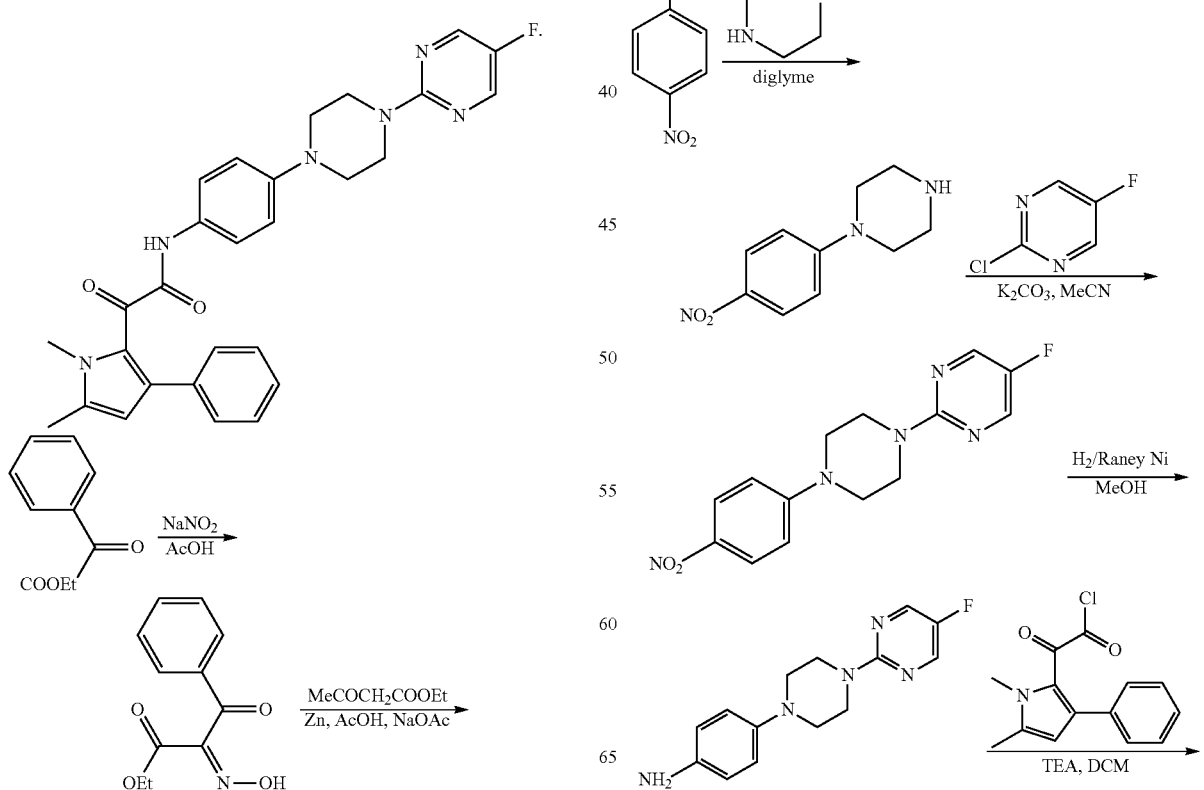

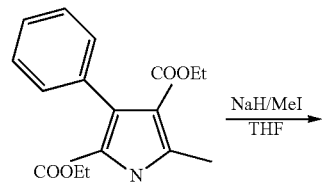

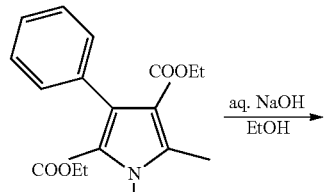

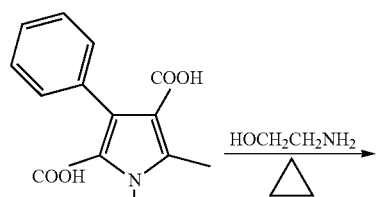

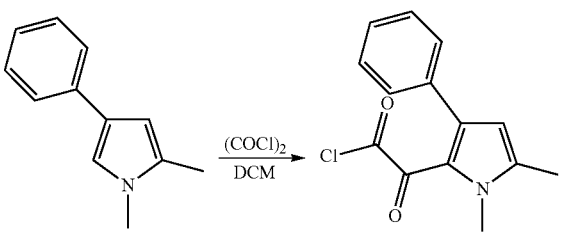

-continued

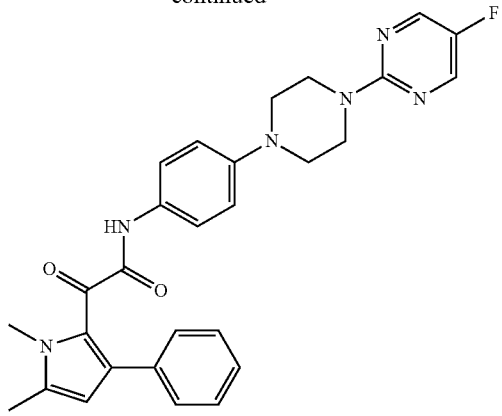

2-Hydroximino-3-oxo-3-phenyl Propionic Acid Ethyl Ester (A)

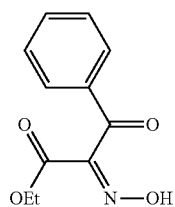 [SMILES: CCOC(=O)/C(=N/O)C(=O)c1ccccc1]

A solution of sodium nitrite (1.07 Kg, 45.62 mol) in water (4 L) was added slowly to a solution of ethyl benzoyl acetate (2 Kg, 10.41 mol) in glacial acetic acid (6 L), at 0-10° C. over a period of 2 h. The product started precipitating during the course of addition. The reaction mass was warmed to room temperature and stirred for a further 1 h. Water (2.5 L) was added and the mixture stirred for a further 1 h. Filtered under suction, washed with water (2 L). The solid was dissolved in chloroform (8 L) and washed with water (2×500 mL), brine solution (2×500 mL), dried over anhydrous sodium sulfate and concentrated in vacuo to dryness to afford 2.0 Kg (86%) of 2-hydroxyimino-3-oxo-3-phenyl propionic acid ethyl ester A as a white solid. [TLC system: Ethyl acetate:Pet ether (3:7); $R_f$ value: 0.28].

5-Methyl-3-phenyl-1H-pyrrole-2,4 dicarboxylic acid diethyl ester (B)

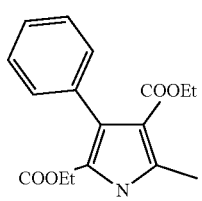 [SMILES: CCOC(=O)c1[nH]c(C)c(C(=O)OCC)c1-c1ccccc1]

A mixture of ethyl acetoacetate (329 g, 2.53 mol), zinc dust (443 g, 6.78 mol) and anhydrous sodium acetate (463 g, 5.65 mol) in glacial acetic acid (800 mL) were heated to 60° C. A solution of A (500 g, 2.26 mol) in glacial acetic acid (1.5 L) was added in three portions under vigorous stirring over a period of ~1 h. The temperature shot up to about 93° C. during the addition. The reaction mixture was maintained at 60-75° C. for 3 h. Additional zinc dust (221 g, 3.39 mol) was added to the reaction mass over 15 min and the mixture was stirred at 60-75° C. for 1 h, cooled to room temperature and filtered the solids. The filtrate was evaporated in vacuo and the residue was co-distilled with toluene (2×500 mL). Water (5 L) and ethyl acetate (1 L) were added to the residue and stirred till two clear layers were obtained. The organic layer washed successively with water (2×500 mL), saturated bicarbonate solution (2×500 mL), brine (2×500 mL) dried over anhydrous sodium sulfate and concentrated to give 360 g of crude gummy product. This was stirred with a mixture of dichloromethane in pet ether (200 mL:1200 mL; 1:6) at room temperature for 15 min, filtered and washed with pet ether (100 mL) to afford 250 g (36%) of 5-methyl-3-phenyl-1H-pyrrole-2,4 dicarboxylic acid diethyl ester B as off-white solid. [TLC system: ethyl acetate:Pet ether (3:7); $R_f$ value: 0.45]. Similarly 1.5 Kg (500 g×3) of A was converted to 500 g [245 g (36%)+255 g (37%)+250 g (36%)] of B in three batches.

1,5-Dimethyl-3-phenyl-1H-pyrrole-2,4-dicarboxylic Acid Diethyl Ester (C)

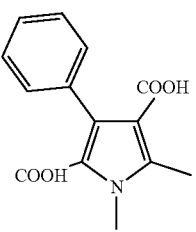 [SMILES: Cc1c(C(=O)O)c(-c2ccccc2)c(C(=O)O)n1C]

A solution of B (1 Kg, 3.322 mol) in dry tetrahydrofuran (4 L) was added to slurry of sodium hydride (60% w/w; 254 g, 6.644 mol) in dry tetrahydrofuran (4 L) at 0° C. over 1 h. The reaction mass was warmed to room temperature and stirred for 1 h and again cooled to 0° C. Methyl iodide (517 mL; 8.305 mol) was added over ½ h and the reaction mixture stirred at room temperature for 18 h. Quenched with ice-water (100 mL) and 1N hydrochloric acid (2 L) was added. The organic layer was separated and the aqueous layer was extracted with dichloromethane (2×500 mL). The combined organic layers were washed successively with brine (2×200 mL), dried over anhydrous sodium sulfate and concentrated to dryness to afford 950 g (91%) of 1,5-dimethyl-3-phenyl-1H-pyrrole-2,4-dicarboxylic acid diethyl ester C as a yellow solid [TLC system: ethyl acetate:Pet ether (3:7); $R_f$ value: 0.56].

1,5-Dimethyl-3-phenyl-1H-pyrrole-2,4-dicarboxylic acid (D)

A solution of sodium hydroxide (1.21 Kg, 30.25 mol) in water (3.6 L) was added to a solution of C (950 g, 3.025 mol) in ethanol (5 L) and heated at reflux for 15 h. Ethanol was evaporated under reduced pressure, the residue was diluted with water (1 L) and chilled to 0° C. Concentrated hydrochloric acid (2 L) was slowly added to adjust pH to ~2, while maintaining temperature below 10° C. and stirred for 1 h. The precipitated solid was filtered, washed with water (1 L) and pet ether (1 L) and dried under vacuum at 60° C., to afford 550 g (70%) of 1,5-Dimethyl-3-phenyl-1H-pyrrole-2,4-dicarboxylic acid D as a white solid. [TLC system: ethyl acetate:Pet ether (3:7); $R_f$ value: 0.15].

1,2-Dimethyl-4-phenyl-1H-pyrrole (E)

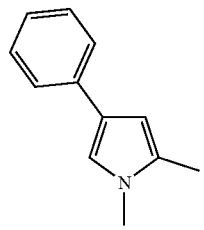

A suspension of E (550 g, 2.123 mol) in ethanolamine (1.5 L) was heated to 175° C. (under $N_2$) and maintained for 1 h. The reaction mixture was cooled to room temperature, diluted with water (500 mL) and extracted with ethyl acetate (3×200 mL). The combined organic layers were washed successively with water (2×100 mL) and brine (2×100 mL), dried over anhydrous sodium sulfate and concentrated in vacuo below 40° C. to give a crude product. Flash chromatography over neutral alumina using 5% ethyl acetate in pet ether as eluent afforded 280 g (77%) of 1,2-dimethyl-4-phenyl-1H-pyrrole E, as a white solid. [TLC system: ethyl acetate:Pet ether (3:7); $R_f$ value: 0.75].

(1,5-Dimethyl-3-phenyl-1H-pyrrol-2-yl)-oxo-acetyl chloride (F)

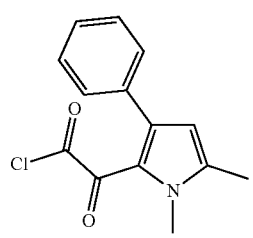 [SMILES: Cc1cc(-c2ccccc2)c(C(=O)C(=O)Cl)n1C]

Oxalyl chloride (116 mL, 1.286 mol) was added slowly to a cooled solution of E (250 g, 1.169 mol) in dry dichloromethane (3×200 mL) at 0° C. The reaction mixture was warmed to room temperature and stirred for 1 h. The solvent was evaporated to dryness in vacuo to afford 340 g (89%) of 1,5-dimethyl-3-phenyl-1H-pyrrol-2-yl)-oxo-acetyl chloride F as a brown oily liquid. [TLC system: ethyl acetate:Pet ether (3:7); $R_f$ value: 0.65]

4-Nitro Phenyl Piperazine (G)

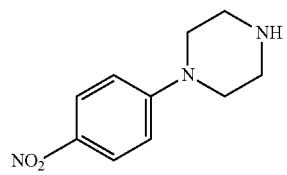 [SMILES: O=[N+]([O-])c1ccc(N2CCNCC2)cc1]

A solution of 1-chloro-4-nitro benzene (650 g, 4.140 mol) in diglyme (1 L) was added to a solution of piperazine (2.84 Kg, 33.12 mol) in diglyme (500 mL) at 100° C. and the resultant mass was stirred at 100° C. for 6 h. The mixture was cooled to 40-45° C., water (5 L) was added; warmed to room temperature and stirred for 1 h. The precipitated solid was filtered, washed with water (1 L), pet ether (500 mL) and dried to give 700 g (81%) of 4-nitro phenyl piperazine G as yellow colour solid. [TLC system: Ethyl acetate:pet ether (3:7); $R_f$ value: 0.70].

5-Fluoro-2-[4-(4-nitro-phenyl)-piperazin-1-yl]-pyrimidine (H)

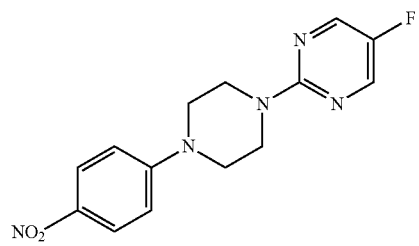

2-Chloro-5-fluoropyrimidine (281 g, 2.12 mol) was added to suspension of 4-nitro phenyl piperazine G (400 g, 1.93 mol) and potassium carbonate (532 g, 3.85 mol) in diglyme (2.5 L), the resulting mixture was stirred at 100° C. for 6 h. On completion the mixture was cooled to 0° C. and filtered, the solid was taken in water (5 L) and stirred for 30 mins. The suspension was filtered, the solid cake was washed with water (1 L), pet ether (1 L) and dried under vacuum to afford 500 g (85%) of 5-fluoro-2-[4-(4-nitro-phenyl)-piperazin-1-yl]-pyrimidine H as yellow colour solid. [TLC system: Ethyl acetate:pet ether (3:7); $R_f$ value: 0.70].

4-[4-(5-Fluoro-pyrimidin-2-yl)-piperazin-1-yl]-phenyl amine (I)

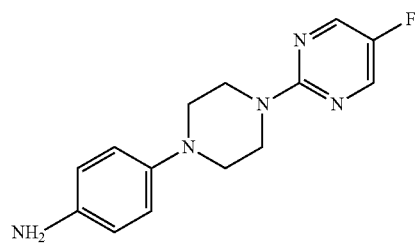 [SMILES: Nc1ccc(N2CCN(c3ncc(F)cn3)CC2)cc1]

A solution of sodium dithionite (1.27 Kg, 7.32 mol) in water (6 L) was added to a suspension of H (500 g, 1.83 mol) and sodium bicarbonate (614 g, 7.32 mol) in methanol (6 L) at 65° C. The resultant mixture was stirred at 65° C. for 2 h. The reaction mass was cooled to 10-15° C. and filtered. The residue was partitioned between water (2 L) and ethyl acetate (5 L), the organic layer was washed with water (2 L), brine (2 L) and dried over anhydrous sodium sulfate. Concentrated in vacuo to afford 290 g (64%) of 4-[4-(5-fluoro-pyrimidin-2-yl)-piperazin-1-yl]-phenyl amine I as solid. [TLC system: Methanol:Chloroform (1:9); $R_f$ value: 0.50].

2-(1,5-Dimethyl-3-phenyl-1H-pyrro-2-yl)-N-{4-[4-(5-fluoro-pyrimidin-2-yl)-piperazin-1-yl]-phenyl}-2-oxo-acetamide

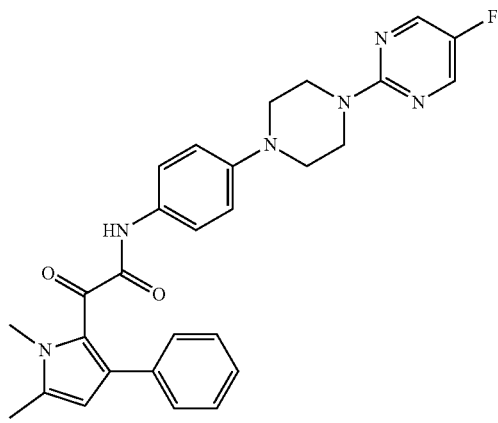 [SMILES: Cc1cc(-c2ccccc2)c(C(=O)C(=O)Nc2ccc(N3CCN(c4ncc(F)cn4)CC3)cc2)n1C]

A solution of F (332 g, 1.27 mol) in dichloromethane (3 L) was added to a stirred solution of I (290 g, 1.06 mol) and triethylamine (294 mL, 2.12 mol) in dichloromethane (3 L) at 0° C. The reaction mixture was warmed to room temperature and stirred for 30 min. The reaction mixture was quenched with water and extracted with dichloromethane (6×500 mL). The combined organic layers were washed successively with saturated sodium bicarbonate solution (1.5 L), water (1 L), brine (1.5 L) and finally dried over anhydrous sodium sulfate. The organic layer was stirred with neutral alumina (1 Kg) at room temperature for 30 min and filtered. The filtrate was concentrated in vacuo to give the crude compound which on washing with diethyl ether (300 mL) and followed by trituration with ethanol (3 L) at 80° C. for 1 h and cooled to room temperature, filtered, washed with ethanol (500 mL) followed by hexane (200 mL) and dried to give 340 g (64%) of 2-(1,5-dimethyl-3-phenyl-1H-pyrro-2-yl)-N-{4-[4-(5-fluoro-pyrimidin-2-yl-piperazin-1yl]-phenyl}-2-oxo-acetamide as yellow color solid. [TLC System: Ethyl acetate:Pet ether (1:1); $R_f$ value: 0.65]. NMR data for 2-(1,5-Dimethyl-3-phenyl-1H-pyrro-2-yl)-N-{4-[4-(5-fluoro-pyrimidin-2-yl)-piperazin-1-yl]-phenyl}-2-oxo-acetamide ($^1$H NMR (400 MHz, CDCl$_3$)) are provided in FIG. 1. The signal was detected in the MS spectrum at 499.1 [M+H]$^+$.

Example 2: Anti-Fungal Activity of the Compound of Formula I

Data demonstrating that 2-(1,5-dimethyl-3-phenyl-1H-pyrrol-2-yl)-N-(4-(4-(5-fluoropyrimidin-2-yl)piperazin-1-yl)phenyl)-2-oxoacetamide inhibits the growth of a wide variety of fungi are presented in the international patent application having application number PCT/GB2015/053546. Information relating to the biological activity of the compound of Formula I is incorporated by reference.

PCT/GB2015/053546 describes experiments comparing the antifungal activity of the compound of Formula I to various reference compounds. The experiments described in PCT/GB2015/053546 show that the compound of Formula I inhibits growth of fungal organisms with MIC (minimum inhibitory concentrations; i.e. the lowest drug concentration that inhibits growth of an organism by >80% compared with a drug free control) as follows:

| Band | MIC/mg/L |
|---|---|
| A | MIC ≤ 0.005 |
| B | 0.005 < MIC ≤ 0.01 |
| C | 0.01 < MIC ≤ 0.02 |
| D | 0.02 < MIC ≤ 0.04 |
| E | 0.04 < MIC ≤ 0.06 |
| F | MIC ≥ 0.06 |

| Organism | MIC band (RPMI medium) |
|---|---|
| A. niger | C |
| A. fumigatus | C |
| A. terreus | A |
| A. flavus | B |
| A. terreus 49 | A |
| A. fumigatus 210 | C |
| S. apiospermum 13486 | D |
| S. apiospermum 15848 | D |
| S. apiospermum 451 | B |
| S. apiospermum 4883 | C |
| S. apiospermum 7935 | C |
| S. apiospermum 8353 | B |
| S. prolificans 18389 | C |
| S. prolificans 206 | D |
| S. prolificans 6322 | D |
| S. species 15849 | E |
| S. apiospermum 13486 | D |
| S. prolifican 201 | D |
| S. prolifican 13486 | D |
| S. prolifican 7935 | C |
| S. prolifican 15848 | D |
| S. prolifican 8353 | B |
| S. prolifican 451 | B |
| S. prolifican 4883 | C |
| S. prolifican 15849 | E |
| S. prolifican 1121 | A |
| S. apiospermum 1124 | A |

The compound of Formula 1 showed also good antifungal activity against *S. dehoogii*, *S. boydii* and *S. aurantiacum*.

PCT/GB2015/053546 also describes experiments in which the compound of Formula I was tested in vivo in a mouse model. The data in that application shows that the compound of Formula I gives excellent efficacy in murine models of invasive aspergillosis, and that the compound of Formula I is able to reduce galactomannan indices in *A. fumigatus* infected mice. The compound of Formula I is also able to increase survival of mice infected with *Lomentospora prolificans* FMR 3569 relative to control experiments using the anti fungal agent voriconazole In the in vivo experiments described in PCT/GB2015/053546, the compound of Formula I was administered orally by gavage. The administration of the compound of Formula I in PCT/GB2015/053546 was not achieved using the formulations of the present invention.

Example 3: PK Experiments—In Vivo Rodent Experiments to Determine Preferred Oral Formulations of the Compound of Formula I Various formulations were investigated in in vivo PK studies in rats to determine the optimal oral formulation for dosing to animals and humans.

The compound of Formula I was administered to rats by IV at a dosage of 10 mg/kg. The vehicle comprised 15% hydroxypropyl beta cyclodextrin (Kelptose HPB parenteral grade), 5% DMSO and water for injection. The formulation was filtered using a ≤0.22 μm polyethersulfone (PES) membrane filter prior to use. The dose volume administered was 5 mL/kg. 0.2 mL blood samples from the sublingual vein under isoflurane anaesthesia were obtained 5 minutes after IV administration and stored in EDTA. Plasma was separated by centrifugation (1500×g, 10 mins, ca. 4° C.) and was frozen at −70° C. prior to analysis. Analysis to calculate plasma concentration of the compound of Formula I was conducted by LC-MS/MS. Typical AUC values ($AUC_{IV}$) of 13500 ng·hr/ml were recorded, corresponding to 100% bioavailability (by definition). The $AUC_{IV}$ value was subsequently used to calculate the bioavailability of example oral formulations as described above.

Formulation 1

A crystalline sample of the compound of Formula I was formulated in PEG300. The formulation was dosed p.o. (gavage) to rats at 10 mg/kg (dose volume=5 mL/kg). 0.2 mL blood samples from the sublingual vein under isoflurane anaesthesia were obtained 15 minutes after oral administration and stored in EDTA. Samples were then taken 0.5, 1, 2, 4, 8, 12 and 24 hours post-dose. PK data (determined as for the IV formulation) revealed $AUC_{PO}$ (0-24 hours) of 6610 ng·hr/ml, corresponding to a bioavailability (F) of 49%.

Formulation 2

A crystalline sample of the compound of Formula I was formulated in a solution of 90% PEG300:10% TPGS (d-α-Tocopheryl polyethylene glycol 1000 succinate). TPGS is a known bioavailability enhancer that acts as a drug solubiliser and a precipitation inhibitor and was incorporated as its presence has proved beneficial in formulations of other insoluble compounds. When dosed p.o. as a solution in a vehicle consisting of PEG300/TPGS at a dose of 150 mg/kg (formulation concentration; 15 mg/mL), the $AUC_{PO}$ (0-24 hours) values in male and female fasted rats were 34271 ng·hr/ml and 76963 ng·hr/ml respectively, equivalent to bioavailability values of 17% and 38% respectively. However, when this formulation was administered for extended periods, side effects of diarrhoea were observed indicating that the formulation would be unsuitable for clinical administration.

Formulations 3 and 4

A crystalline sample of the compound of Formula I was micronised by jet milling to a final particle size of D(v0.9)= 6.7 μm, and subsequently suspended in a mixture of HPMC (75%) and SDS (sodium dodecyl sulphate 0.05%). This formulation (formulation 3) was dosed p.o. to male and female rats at 150 mg/kg. PK experiments gave $AUC_{PO}$ (0-24 hours) values of 9004 ng·hr/ml and 26286 ng·hr/ml for male and female rats respectively, equivalent to a bioavailability of 4.5% and 13% respectively.

The compound of Formula I was nanonised in a similar manner and formulated in HPMC/SDS as for formulation 3 (to give formulation 4), and was administered to male and female rats p.o. PK experiments gave $AUC_{PO}$ (0-24 hours) values of 17785 ng·hr/ml and 40272 ng·hr/ml in male and female rats respectively, equivalent to a bioavailability of 9% and 20%, respectively.

Neither formulation 3 nor formulation 4 yielded adequate bioavailability of the compound of Formula I. Furthermore, PK experiments revealed that the time for maximum plasma concentration of the compound of formula I ($T_{max}$) was significantly delayed suggesting delayed/incomplete absorption.

Formulation 5

The compound of Formula I was formulated with hydroxypropyl methyl cellulose acetate succinate (HPMCAS) (10% w/w compound of Formula I:90% HPMCAS). The formulation was spray-dried from a solution of 3:1 v/v dichloromethane:methanol. The formulation was administered p.o. to male and female rats at a dose of 10 mg/kg in 20 mM phosphate buffer (suspension). PK experiments gave $AUC_{PO}$ (0-24 hours) values of 13202 ng·hr/ml and 27774 ng·hr/ml in male and female rats, respectively, indicating a bioavailability >95% in both sexes.

Unlike formulation 2, formulation 5 was tolerated by both male and female rats with no GI tract disturbances. This allowed toxicological studies to be performed over 1-3 months. Formulation 5 was well tolerated by both male and female rats over this period.

Comparison of Formulation 2 and Formulation 5

A comparison of the results of PK experiments conducted using formulations 2 and 5 was conducted at equivalent dosages (50 mg/kg) dosed p.o. twice daily (BID) for 28 days. These data show that better exposure was obtained using formulation 5 as compared to formulation 2, with the further benefit of the absence of negative effects on the GI tract associated with formulation 2.

| Formulation | Cmpd of Formula I/Dose | Sex | $AUC_{PO}$ ng · hr/ml Day 1 | Day 28 |
|---|---|---|---|---|
| 2 | 50 mg/kg | Male | 19880 | 23280 |
|  |  | Female | 39400 | 92390 |
| 5 | 50 mg/kg | Male | 28860 | 44880 |
|  |  | Female | 43440 | 149700 |

Example 4: PK Experiments—In Vivo Cynomolgus Monkey Experiments to Determine Preferred Oral Formulations of the Compound of Formula I Various formulations were investigated in in vivo PK studies in cynomolgus monkeys to determine the optimal oral formulation for dosing to animals and humans.

The compound of Formula I was administered to male and female cynomolgus monkeys by IV at a dosage of 10 mg/kg. The IV formulation was as described in Example 3. PK experiments gave typical AUC values ($AUC_{IV}$) of 18000 ng·hr/ml. The $AUC_{IV}$ value was subsequently used to calculate the bioavailability of example oral formulations as described above.

Formulation 2

Studies were conducted using Formulation 2 as described above. The compound of Formula I was administered p.o. to male and female cynomolgus monkeys at a dose level of 10 mg/kg. (dose volume 5 mL/kg). 2 mL blood samples were obtained 5 minutes via femoral puncture (vein/artery) into commercially available $K_2$EDTA tubes using 23G needles coupled to a suitable syringe. Samples were taken 0.25, 0.5, 1, 2, 4, 8, 12 and 24 hours after administration of the formulation. Blood samples were kept on ice until centrifugation at 1600×g (10 mins, ca. 5° C.) to separate plasma. Analysis to calculate plasma concentration of the compound of Formula I was conducted by LC-MS/MS. PK experiments gave $AUC_{PO}$ (0-24 hours) values of 14915 ng·hr/ml and 8192 ng·hr/ml in male and female subjects, respectively, indicating a bioavailability of 83% and 46% in males and females, respectively.

Unfortunately, gastrointestinal problems (notably diarrhoea) as observed in experiments in rats (see Example 3 above) were noted also for cynomolgus monkeys. Studies of 1 month duration with the PEG/TPGS vehicle showed that diarrhoea was a major problem despite the use of anti-diarrhoeal medication (Diosmectite; "Smecta", 1 bag (3 g) per animal 4 hours post-dose). These studies showed that despite promising oral bioavailability of the compound of Formula I, formulation 2 was unlikely to be suitable for clinical administration.

Formulation 5

Studies were conducted using Formulation 5 as described in Example 3. The compound of Formula I was administered p.o. to male and female cynomolgus monkeys at a dose level of 10 mg/kg (dose volume: 5 mg/kg; formulation concentration 2 mg/mL of the compound of Formula I, corresponding to 20 mg/mL of the spray-dried particles)

The particles produced as described for Formulation 5 were suspended in different buffer compositions/volumes. PK experiments as described above gave $AUC_{PO}$ (0-24 hours) values as follows:

| Sex | Dose/mg/kg | Vehicle | $AUC_{PO}$ (0-24 hours)/ ng · hr/ml |
|---|---|---|---|
| Male | 10 | 10 ml/20 mM phosphate buffer | 16804 |
| Female | 10 | 10 ml/20 mM phosphate buffer | 20871 |
| Male | 10 | 5 ml/40 mM phosphate buffer | 26112 |
| Female | 10 | 5 ml/40 mM phosphate buffer | 12684 |

As can be seen, when low buffer salt concentrations (20 mM) and high buffer volumes (10 mL) were used, or when low buffer volumes (5 mL) but higher buffer strengths (40 mM) were used, high $AUC_{PO}$ (0-24 hours) values were observed. Under these conditions, bioavailability >90% was observed using 10 ml of 20 mM phosphate buffer and bioavailability >70% using 5 ml of 40 mM phosphate buffer. (Slight variation in the results obtained using female subjects dosed with 5 ml of 40 mm buffer was observed which accounts for the apparently poorer bioavailability in this subject group).

Studies carried out with formulation 5 at a variety of doses in cynomolgus monkeys revealed a complete lack of gastrointestinal side effects; the formulation is thus much better tolerated in mammals than formulation 2 described above. High drug levels were obtained after repeat dosing, with improved dose proportionality observed between doses.

Comparison of Formulation 2 and Formulation 5

A comparison of the results of PK experiments conducted using formulations 2 and 5 was conducted at equivalent dosages (50 mg/kg) dosed p.o. twice daily (BID) for 14 days. These data show that better exposure was obtained using formulation 5 as compared to formulation 2, with the further benefit of the absence of negative effects on the GI tract associated with formulation 2.

| Formulation | Cmpd of Formula I/Dose | Sex | $AUC_{PO}$ ng · hr/ml Day 1 | Day 14 |
|---|---|---|---|---|
| 2 | 50 mg/kg | Male | 50460 | 59590 |
|   |          | Female | 32160 | 91250 |
| 5 | 50 mg/kg | Male | 57200 | 86745 |
|   |          | Female | 48810 | 110500 |

The above data obtained in both rat and cynomolgus monkey shows that when the compound of Formula I is formulated in the form of Formulation 5 described above, excellent pharmacokinetics in both rat and cynomolgus monkey is observed. The formulation is well tolerated and is especially beneficial compared with solvent based vehicles such as PEG/TPGS due to the absence of observed GI symptoms which would be likely to require intervention with antidiarrheal treatments if used clinically. There is also better dose proportionality in AUC and Cmax using this formulation compared with solvent based formulations.

Formulation 6

The compound of Formula I was formulated in a solution of 25% DMSO: 75% PEG300 (% v/v) (concentration of compound in vehicle: 2 mg/mL). The formulation was administered p.o. to male and female cynomolgus monkeys at a dose of 10 mg/kg (administered dose volume: 5 mL/kg). 2 mL blood samples were obtained 5 minutes via femoral puncture (vein/artery) into commercially available $K_2EDTA$ tubes using 23G needles coupled to a suitable syringe. Samples were taken 0.25, 0.5, 1, 2, 4, 8, 12 and 24 hours after administration of the formulation. Blood samples were kept on ice until centrifugation at 1600×g (10 mins, ca. 5° C.) to separate plasma. Analysis to calculate plasma concentration of the compound of Formula I was conducted by LC/MS-MS. PK experiments gave $AUC_{PO}$ (0-24 hours) values of 2900 ng·hr/ml and 1480 ng·hr/ml in male and female subjects, respectively, indicating a bioavailability of 16% and 8% in males and females, respectively.

Formulation 7

A lipid based formulation (Catalent) intended to assist solubilisation (and thus increase bioavailability) of the compound of Formula I was developed and tested in cynomolgus monkeys as described above. This formulation was administered p.o. to male and female cynomolgus monkeys at a dose of 10 mg/kg. PK experiments gave $AUC_{PO}$ (0-24 hours) values of 3282 ng·hr/ml and 1924 ng·hr/ml in males and females, respectively, indicating very low bioavailability values of 18% and 11%, respectively.

Example 5: PK Experiments—In Vivo Human Trials

Studies were conducted using a spray-dried formulation in accordance with the compositions of the inventions. The formulation consisted of 20% of the compound of Formula I/80% HPMCAS suspended in 20 mM phosphate buffer as described for formulation 5 in Example 4. Blood samples were taken following dosage of the formulation and plasma concentrations of the compound of Formula I were determined as described above.

Initial experiments were conducted to determine the effect of varying the administered dose of the formulation. Results are presented in the following Table.

| Dose (mg/kg) | $T_{max}$[#] (h) | $C_{max}$ (µg/mL) | $AUC_{0-12}$ | $AUC_{0-24}$ (µg · h/mL) | $AUC_{0-t}$ | $ALC_{0-\infty}$ | $t_{1/2}$ (h) | CL/F (mL/h)/kg | $C_{12}$[+] (µg/mL) | $C_{24}$[+] | MRT (h) | $V_{ss}$/F (L/kg) |
|---|---|---|---|---|---|---|---|---|---|---|---|---|
| 2 | 1.25 | 0.913 | 4.36 | 6.84 | 11.68 | 12.18 | 23.3 | 190 | 0.154 | 0.205 | 29.5 | 5.23 |
| 4 | 2.5 | 2.30 | 13.30 | 19.24 | 40.51 | 46.67 | 37.0 | 112 | 0.552 | 0.547 | 47.6 | 4.45 |
| 6 | 3.5 | 3.67 | 19.85 | 32.09 | 64.72 | 69.44 | 29.2 | 95 | 0.814 | 1.018 | 40.7 | 3.79 |
| 8 | 4.0 | 5.32 | 28.38 | 41.76 | 81.86 | 88.20 | 32.3 | 94 | 1.290 | 1.254 | 44.1 | 4.05 |
| 10 | 3.0 | 5.79 | 28.80 | 44.14 | 79.21[$] | 99.14 | 31.1 | 111 | 1.352 | 1.338 | 42.0 | 4.34 |

[#]Median values.
[+]Concentrations at 12 and 24 h post-dose (for potential repeat dose purposes).
[$]$AUC_{0-t}$ values only from 0-72 h at present to prevent unblinding.

Figure 2:
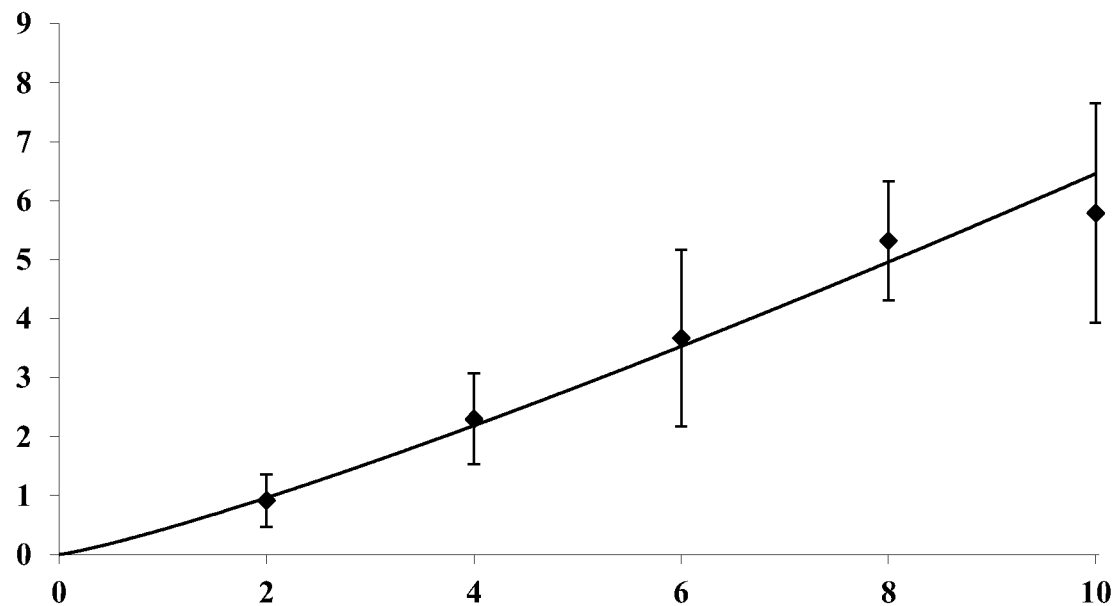
FIG. 2 shows pharmacokinetic data obtained in human trials of a formulation of the compound of Formula I according to the invention as described in Example 5. y-axis: Plasma $C_{max}$ (µg/mL); x-axis: dose of the compound of Formula I (mg/kg).
Figure 3:
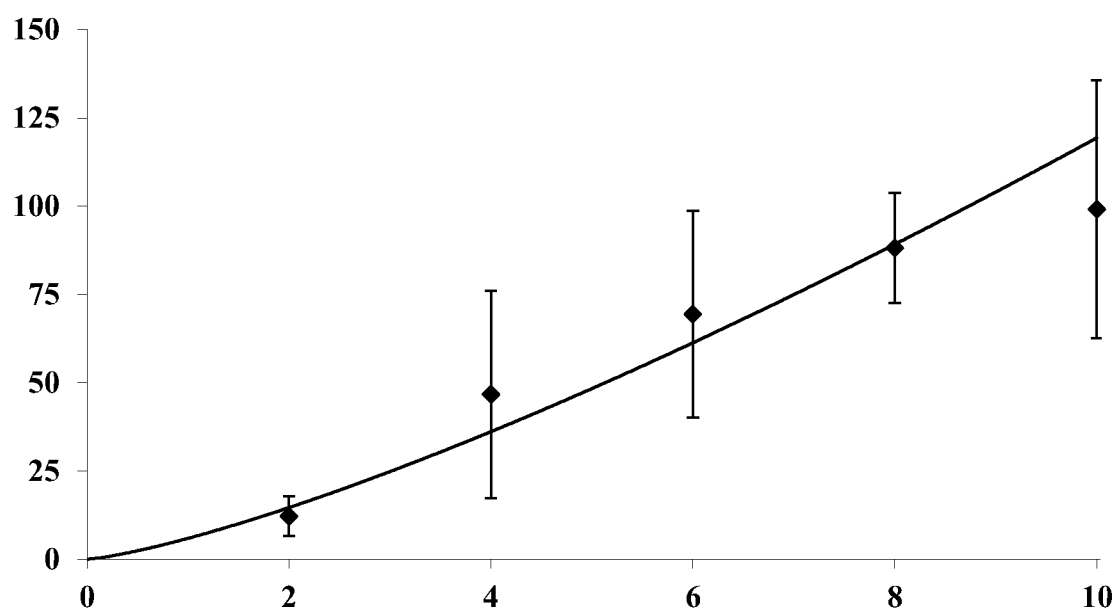
FIG. 3 shows pharmacokinetic data obtained in human trials of a formulation of the compound of Formula I according to the invention as described in Example 5. y-axis: Plasma $AUC_{0-\infty}$ (µg·h/mL); x-axis: dose of the compound of Formula I (mg/kg).

In the preceding table: $T_{max}$=time of observed maximum concentration of the compound of Formula I; $C_{max}$=observed maximum concentration; $AUC_{A-B}$=area under the PK plasma curve vs time curve, wherein A is time=0 hours and B=time to which curve determined; $t_{1/2}$=apparent terminal elimination half-life; CL=clearance; $C_n$ (n=12, 24)=concentration of compound of Formula I at indicated time point; MRT=mean residence time; $V_{SS}$=volume of distributation at steady-state Plots of $C_{max}$ and $AUC_{0-\infty}$ as a function of administered dose revealed good dose proportionality ($C_{max}$: proportionality=1.18; AUC: proportionality=1.30) as shown in FIGS. 1 to 3. Excellent bioavailability of ca. 95%+ was observed.

The invention claimed is:

1. A pharmaceutical composition suitable for oral administration comprising (i) spray-dried particles of a compound of Formula I or a pharmaceutically acceptable salt thereof

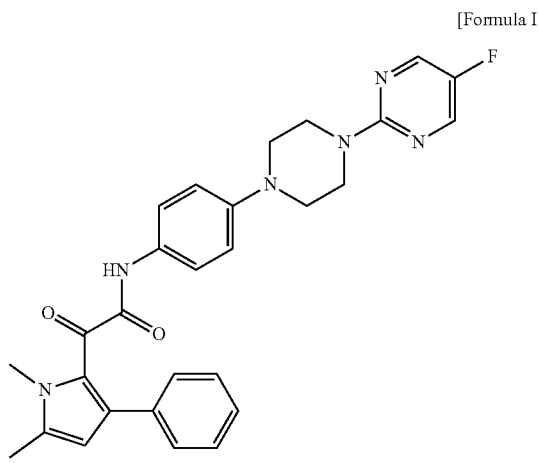

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide, and (ii) one or more excipients comprising hydroxypropyl methyl cellulose acetate succinate (HPMCAS).

2. The pharmaceutical composition according to claim 1, wherein the mass ration of the compound of Formula I or the pharmaceutically acceptable salt thereof to the one or more excipients is from 1:15 to 1:2.

3. A pharmaceutical composition suitable for oral administration comprising (i) spray-dried particles of a compound of Formula I or a pharmaceutically acceptable salt thereof

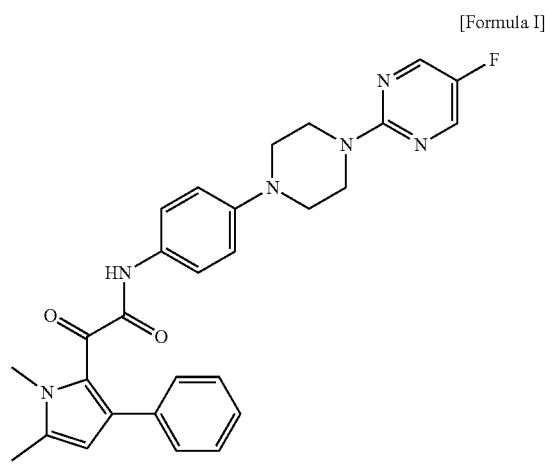 [SMILES: Cc1cc(-c2ccccc2)c(C(=O)C(=O)Nc2ccc(N3CCN(c4ncc(F)cn4)CC3)cc2)n1C]

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide, wherein the particles are obtained by spray-drying from a solution comprising an organic solvent selected from the group consisting of dichloromethane, methanol, and mixtures thereof.

4. A pharmaceutical composition suitable for parenteral administration comprising:
(i) a compound of Formula I or a pharmaceutically acceptable salt thereof

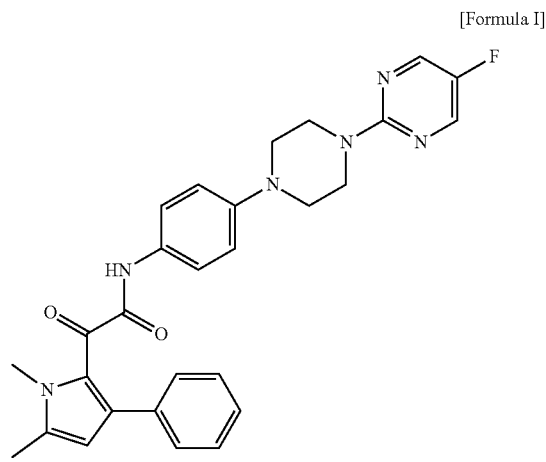 [SMILES: Cc1cc(-c2ccccc2)c(C(=O)C(=O)Nc2ccc(N3CCN(c4ncc(F)cn4)CC3)cc2)n1C]

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide (ii) cyclodextrin or modified cyclodextrin; and
(iii) polyethylene glycol.

5. The pharmaceutical composition according to claim 4, comprising:
from 10 wt % to 40 wt % of cyclodextrin or modified cyclodextrin;
from 10 wt % to 40 wt % of polyethylene glycol;
or a mixture thereof.

6. A pharmaceutical composition according to claim 4, wherein the cyclodextrin or modified cyclodextrin is hydroxy propyl beta cyclodextrin.

7. A pharmaceutical composition according to any of claims 4, wherein the polyethylene glycol is PEG300 or PEG400.

8. A pharmaceutical composition according to any one of claims 4, further comprises polyvinyl pyrrolidone (Povidone).

9. The pharmaceutical composition according to claim 4, wherein the compound of Formula I, or the pharmaceutically acceptable salt thereof, is present at a concentration of from 1 mg/mL to 10 mg/mL.

10. A pharmaceutical composition according to any one of claim 4, further comprises one or more pharmaceutically acceptable carriers, excipients, diluents, adjuvants, or mixtures thereof.

11. A pharmaceutical composition according to any one of claim 4, comprising:
4 mg/mL (relative to the final volume of the composition) of the compound of Formula I;
25 wt % of hydroxy propyl beta cyclodextrin;
25 wt % of PEG400;
1 wt % of polyvinyl pyrrolidone (Povidone);
phosphoric acid in sufficient amount to adjust the pH of the pharmaceutical composition to pH 5.0; and
water to 100%.

12. A method of producing a pharmaceutical composition comprising a compound of Formula I or a pharmaceutically acceptable salt thereof

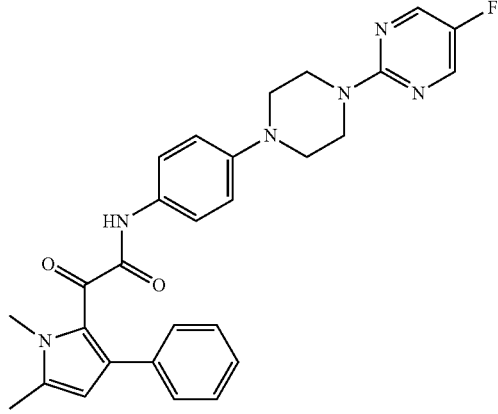

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide, wherein said method comprises:
i) dissolving one or more excipients in a solvent;
ii) adding the compound of Formula I, or the pharmaceutically acceptable salt thereof, to the solution produced in step (i); and
iii) spray drying the solution produced in step (ii),
wherein:
the one or more excipients comprises hydroxypropyl methyl cellulose acetate succinate (HPMCAS);
the solvent is a mixture of dichloromethane and methanol, wherein the volume ratio of dichloromethane to methanol is from 5:1 to 1:1;
the concentration of hydroxypropyl methyl cellulose acetate succinate (HPMCAS) in the solvent is from 5% to 20% w/v; and
the compound of Formula I, or the pharmaceutically acceptable salt thereof, is added to the solution produced in step (i) to give a concentration of 0.5% to 10% by mass.

13. A pharmaceutical composition comprising (i) spray-dried particles of a compound of Formula I or a pharmaceutically acceptable salt thereof

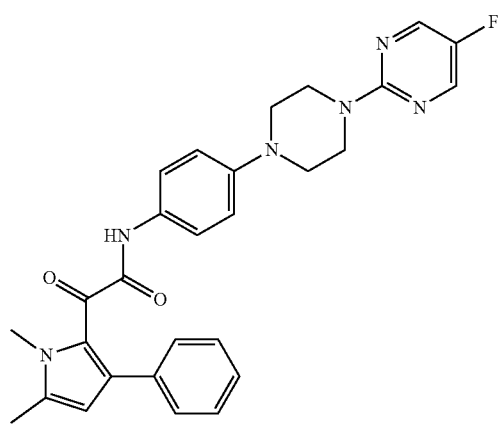

[Formula I]

2-(1,5-dimethyl-3-phenyl-1H-pyrrol-2-yl)-N-(4-(4-(5-fluoropyrimidin-2-yl)piperazin-1-yl)phenyl)-2-oxoacetamide, and (ii) a cyclodextrin or modified cyclodextrin, wherein said pharmaceutical composition is in the form of a solution, syrup, emulsion or suspension.

14. The pharmaceutical composition according to claim 13, wherein the cyclodextrin or modified cyclodextrin is hydroxy propyl beta cyclodextrin.

15. The pharmaceutical composition according to claim 13, wherein the compound of Formula I, or the pharmaceutically acceptable salt thereof, is present at a concentration of from 1 mg/mL to 10 mg/mL.

16. A method of preventing or treating fungal infection in a human or animal subject in need thereof, said method comprising administering to the human or animal subject a therapeutically effective amount of the pharmaceutical composition according to claim 4.

17. The pharmaceutical composition according to claim 13, further comprising one or more excipients, wherein the mass ratio of the compound of Formula I or the pharmaceutically acceptable salt thereof to the one or more excipients is from 1:100 to 1:1.

* * * * *

UNITED STATES PATENT AND TRADEMARK OFFICE
CERTIFICATE OF CORRECTION

PATENT NO. : 10,973,821 B2
APPLICATION NO. : 16/303999
DATED : April 13, 2021
INVENTOR(S) : Law et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 124 days.

Signed and Sealed this
Thirty-first Day of January, 2023

Katherine Kelly Vidal
*Director of the United States Patent and Trademark Office*